United States Patent [19]

Fischell

[11] 4,373,527

[45] Feb. 15, 1983

[54] IMPLANTABLE, PROGRAMMABLE MEDICATION INFUSION SYSTEM

[75] Inventor: Robert E. Fischell, Silver Spring, Md.

[73] Assignee: The Johns Hopkins University, Baltimore, Md.

[21] Appl. No.: 34,155

[22] Filed: Apr. 27, 1979

[51] Int. Cl.³ ............................................. A61M 7/00
[52] U.S. Cl. ................................... 128/260; 128/903; 128/DIG. 12; 128/DIG. 13
[58] Field of Search ............... 128/214 E, 214 F, 260, 128/419 E, 419 PG

[56] References Cited

U.S. PATENT DOCUMENTS

| | | | |
|---|---|---|---|
| 3,727,616 | 4/1973 | Lenzler | 128/419 E |
| 3,731,681 | 5/1973 | Blackshear et al. | 128/260 |
| 4,049,004 | 9/1977 | Walters | 128/419 PG |
| 4,055,175 | 10/1977 | Clemens et al. | 128/260 |
| 4,077,405 | 3/1978 | Hoerton et al. | 128/260 |
| 4,146,029 | 3/1979 | Ellinwood, Jr. | 128/260 |

OTHER PUBLICATIONS

Crone, J. et al., "A Programmable Infusion Pump Controller", (Abstract) 30th ACEMB, Los Angeles, Nov. 5-9, 1977, p. 95.
Crone, J. et al., "A Programmable Infusion Pump Controller", (Complete Paper) 30th ACEMB, Los Angeles, Nov. 5-9, 1977.
Albisser, A. M., "Studies with an Artificial Endocrine Pancreas", Arch. Internal Medicine, vol. 137, May 1977.
Stomm, Walter E., "Infections Related to Medical Devices", Ann. of Internal Medicine, 89, 1978.
Irsigler, K. et al., "Long-Term Insulin Therapy with Portable Dosage Regulating Apparatus", Diabetes, Mar. 1979, vol. 28.
Pickup, J. E. et al., "Continuous Sub-Q Insulin Infusion: An Approach to Achieving Normoglycemia", Brit. Med. Jrnl., vol. 1, 1978.

Rolide, T. D. et al., "One Year of Heparin Anti-Coag.", Minn. Med., Oct. 1977.
Rolide, T. D. et al., "Protracted Parent. Drg. Infus. in Ambul. Patents Using Implant Infus. Pump", Trans.-Am. Soc. Art. Int. Organ., vol. 22, Oct. 1977.
Kaplan, W. D. et al., "Intra-Arterial Radionuclide Infusion", Cancer Treatment Reports, vol. 62, May 1978.
Spencer, W. J., "For Diabetics: An Electronic Pancreas", IEEE Spectrum, vol. 15, Jun. 1978.
Clemens, A. A. et al., "The Devel. of Biostator, A Glucose-Controlled Insulin Infusion System", Hormones & Metal Research Supp., vol. 7, 1977.

Primary Examiner—Kyle L. Howell
Assistant Examiner—Francis J. Jaworski
Attorney, Agent, or Firm—Robert E. Archibald; Marc A. Block; Samuel L. Sachs

[57] ABSTRACT

An implantable programmable medication infusion system comprises an implantable portion (2) having a medication reservoir (10) at below body pressure and isolated at its input from the body in which it is implanted by an antechamber (8) the pressure integrity of which is checked before filling the medication reservoir (10). Safety features include a leak detector (35), inlet and outlet valves (14 and 212) used with flow impeding filters (12 and 218), and a maximum allowable pressure in a pulsatile bellows pump (202) all of which prevent undesired infusion of medication. Medication flow from the pulsatile bellows pump (202) is in response to programming commands from a drug programming system (1) and processed in an electronics section (30) which uses the commands to program memory units (320 and 322) and to request pulses of medication. Hardwired limit controls (324 and 326) prevent excessive dosage requests from reaching the pulsatile bellows pump (202). For patient convenience and safety, the memory units (320 and 322) are programmed with running integral limits. A record of medication dispensing can be communicated to a physician by means of a telemetry transmitter (336) which sends signals by telemetry to the communications head (300) which information is displayed on the drug programming unit (3).

642 Claims, 8 Drawing Figures

FRONT VIEW

REAR VIEW

IMPLANTABLE, PROGRAMMABLE MEDICATION INFUSION SYSTEM

FIELD OF THE INVENTION

The present invention relates to the filed of dispensing medication to a living being. Although mainly intended for use by human patients requiring infusions of a drug, such as insulin, glucose, heparin, or any of various other chemotherapeutic agents, the invention extends to use in any living body (such as domestic animals) and to the infusion of any liquid (such as blood) or colloidal suspension, or gas or granulated solid, which may provide a curative or healing effect. Although a principal use envisioned is for implantable devices, it is also envisioned that it could be used external to a living being for the infusion of medication.

TECHNOLOGICAL CONTEXT OF THE INVENTION

Various techniques and devices have been suggested and are currently under study which address the problem of dispensing a drug or other medicative liquid into a living body. Of these techniques and devices, however, redundant safety features and flexibility achieved by programming dosage inputs are rarely contemplated.

One liquid infusion device discussed in U.S. Pat. No. 4,077,405 by Haerton et al discloses a controllable dosing arrangement which provides for human operator interaction. A syringe forces liquid through a pressure valve into a supply reservoir and a bellows pump forces drug from the reservoir through a flow limiter into the body. Haerton et al teaches an "overpressure" technique where liquid in the reservoir is at a pressure above that at the discharge point. This device fails to address various safety problems such as leakage, excessive pumping, and excessive requests for drug. In particular, should the input control valve in Haerton et al leak, a flood of liquid would enter the body because of the pressure differential and the lack of any back-up safety mechanism. No provision for detecting leaks in the device, for signalling malfunctions, for restricting the number of or quantity of drug doses, or for monitoring proper operation of the device is suggested.

Like Haerton et al, U.S. Pat. No. 3,692,027 by Ellinwood teaches an implanted, self-powered drug dispenser having a bellows pump which is fed through and expels drug through valves, in particular one-way valves. The Ellinwood devices is not programmable; it varies dosage by opening and closing portals or selecting a dose or medication from one of a plurality of pumps having different dosage volumes and/or different medications stored therein. Safety redundancy such as pressure integrity checks during filling, leakage problems, patient and doctor interaction with the dispenser, and dosage input programming are not considered.

An invention of Blackshear (U.S. Pat. No. 3,731,681) shows another infusion pump without redundant safety features. While disclosing an implanted bellows pump arrangement fed through a self-sealing plug, Blackshear does not look for pressure integrity before filling the device with drug. Further, because there is no input valve and because the pressure in the device is above that of the body in which it is implanted, leakage in Blackshear can be dangerous. Further, like Haerton et al and Ellinwood, Blackshear does not disclose an antechamber which can serve various safety purposes.

Richter (U.S. Pat. No. 3,894,538) considers, in a medicine supplying device, one safety feature: an exit plug for preventing contaminants from entering the device and for limiting drug outflow. The flow from the Richter device does not provide a smooth pulsatile flow of drug which is infused over a relatively long period. It further fails to disclose any means for reliably controlling or varying the flow rate.

A device by Jacob (U.S. Pat. No. 4,033,479), like other techniques, provides a bellows pump chamber which maintains drug at a "constant internal pressure." A valve opens to release drug into a body and the bellows varies the chamber volume to maintain constant pressure. It is not of importance to Jacob how much pressure there is in the chamber—it is above body pressure—but, rather, the concern is to keep pressure constant. Leakage out from the valve and the spurting of drug into the body under relatively high constant pressure would appear to be problems inherent in the Jacob device.

Several recent publications have also underscored the need for an implantable medication infusion device. Two articles by Rohde et al ("One Year of Heparin Anticoagulation;" *Minnesota Medicine;* October, 1977 and "Protracted Parenteral Drug Infusion in Ambulatory Subjects Using an Implantable Infusion Pump"; *American Society for Artificial Internal Organs Transactions, Volume XXIII;* 1977) describe an implantable infusion pump which comprises a hollow disk separated into two chambers by a bellows. A volatile fluorocarbon in the outer chamber forces drug from the inner chamber through a filter and catheter into a patient. Filling of the inner chamber is accomplished by penetrating a self-sealing septum which apparently forms a wall of the inner chamber. The condensation of the fluorocarbon during filling, and the subsequent vaporization of the fluorocarbon using body heat provides energy for cyclical pumping. No antechamber, no check for pressure integrity before filling or during operation, no programming means, and no patient or doctor interaction with the device are contemplated.

Finally, an article by Spencer ("For Diabetics: an electronic pancreas;" *IEEE-Spectrum;* June, 1978) discusses current trends in the implantable drug pump field. Programming the rate of drug flow over time depending on food intake is mentioned. Efforts in the development of an implantable bellows pump are also discussed. Spencer further mentions the use of alarm sounds if a pump fails to provide drug in accordance with the preprogrammed rate. The Spencer article generally discusses drug dispenser technology but fails to address many specific problems. As in other cited work, redundant safety features such as an antechamber; leak detection; distinctive subcutaneous stimulation to indicate various device malfunctions; safe method of programming the device regardless of work, food-intake, or time schedules; and maintaining the reservoir pressure below ambient body pressure so that a leak would result in body fluids being inadvertently released into the device as opposed to a fatal dose of drug entering the body (at a high, constant pressure) are not considered.

SUMMARY OF THE INVENTION

In a field where safety and reliability are paramount, the present invention provides extensive redundancy to prevent device failure.

The present medication infusion system provides an antechamber which is normally filled with saline solution to act as a buffer between the medication intake point and the major medication reservoir in the device. The reservoir may contain a fatal amount of drug or other medication. It is thus isolated from the body by a filter, one-way inlet valve, the saline-containing antechamber and a septum providing a self-sealing opening to the antechamber. Further, the reservoir is at a pressure below the ambient body pressure. Thus, even if the inlet valve and septum leak, body fluids would enter the antechamber and slowly ooze into the reservoir through the flow-impeding filter. Any other leak of medication from the reservoir or leakage of body fluid through the outer shell of the implanted device would be sensed by a fluid detector outside the reservoir. Similar safety back-ups are provided at the outlet output of the reservoir which is provided with two one-way values and a filter.

The outlet, however, also is provided with a deformable wall which combines with the outlet filter to yield an exponentially decaying flow of medication. This smooth flow over a long, predetermined period provides enhanced safety and flow control. The deformable wall serves the function of an accumulator and the output filter provides the function of a flow resistor or restrictor; thus the deformable wall provides the "C" and the filter the "R" of an "RC" time constant for the decrease of flow after a pulse of medication has been delivered into an outlet chamber prior to infusion into the body via the RC network. Also at the outlet is an element for correlating medication requests with medication dispensing, thus providing an operational indicator and safety feature.

Also, for safety, a filling procedure is provided which insures that medication is not injected into the device until pressure integrity at the input is determined.

In the mechanical pump itself, the amount of medication pulsing it can provide is restricted by a pressure limit intrinsic in the pump design.

In programming the present system, convenience and safety are again major concerns. A flexible, maximum running integral program for limiting medication dosage inputs communicated by a patient satisfies not only a patient's need for proper amounts of medication but also satisfies a variable work and eating schedule requirement of the patient and can provide a safe, proper medication schedule even though the patient experiences time zone or work schedule changes. In addition to a programmable rate of medication input, a hardwired limit is also included. If requests exceed the limits set by the program, the hardwired limits will inhibit the pulsing of excessive medication into the patient.

Finally, the system provides a history of medication infusion which a physician can read out through telemetry means. This telemetry means is also used to program and check the system.

DESCRIPTION OF THE DRAWINGS

FIG. 7 shows a front view illustrating sample apparatus for selecting dosage depending on meal size and recognized body condition factors. FIG 8 shows a rear portion which provides information relative to the last programming of the patient programming unit.

DESCRIPTION OF THE INVENTION

Figure 1:
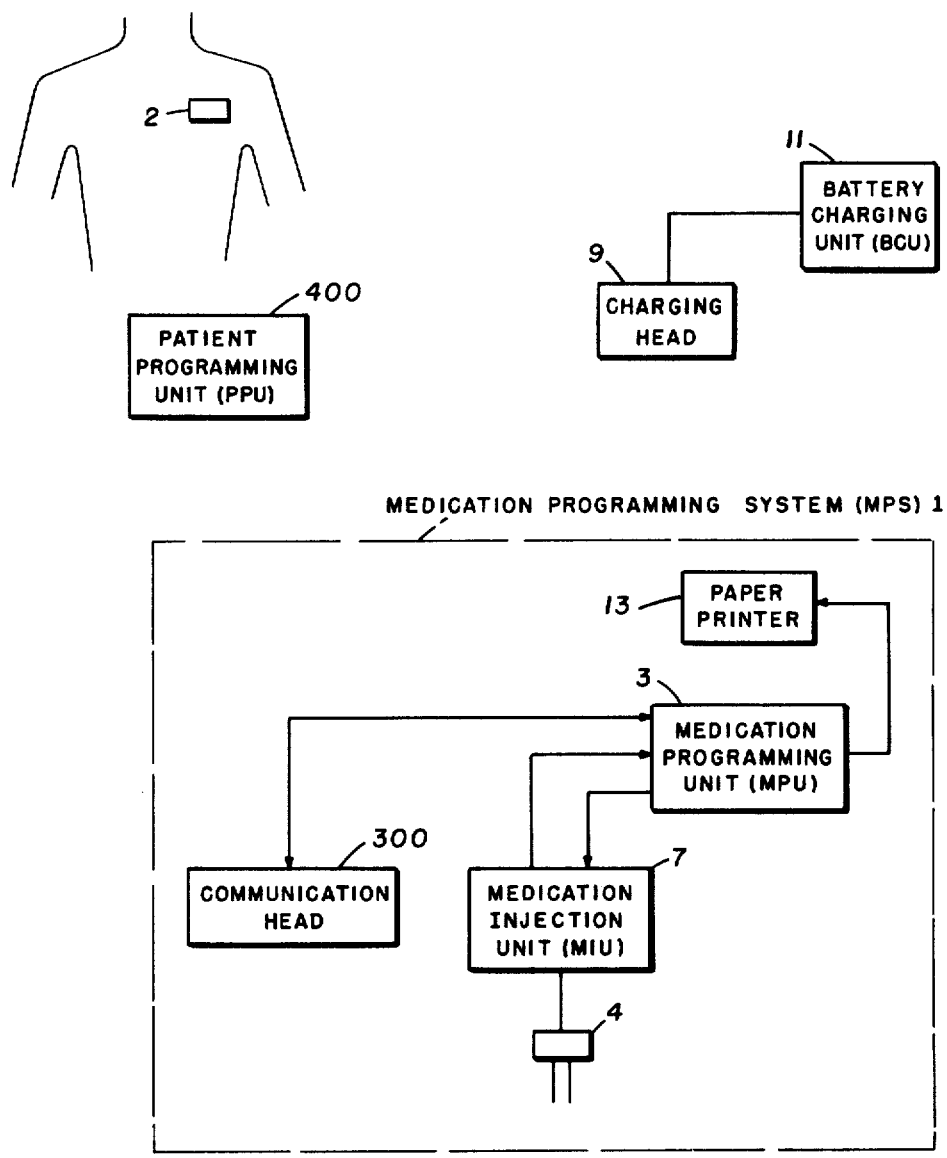
FIG. 1 illustrates a general block diagram of the entire medication infusion system of the present invention.

Referring to FIG. 1, the various portions of the implantable programmable medication infusion system are shown. An implantable portion 2 in a patient's body can be programmed either by the medication programming system 1 or by the patient's programming unit 400. Commands from the medication programming system 1 emitted from the communication head 300 are transmitted to electronics in the implantable portion 2 in order to program and effectuate the infusion of medication into the body in a safe, controlled fashion. The medication programming system 1 is also capable of reading information out of the implantable portion 2 concerning the amount of medication dispensed over a specified time period and furthermore the medication programming system 1 is capable of calibrating the per pulse of medication of the implantable portion 2. A medication injection unit 7 is connected to a double hypodermic syringe 4 which is used to provide medication to an implantable medication reservoir 18 (shown in FIGS. 2 and 3) included within the implantable portion 2. Fill commands to the medication injection unit 7 emanate from a medication programming unit 3. A patient's programming unit 400 is controlled by the user to request doses of medication. The dosage requests are controlled by safety units embodied in fixed hardware elements and programmable elements found in the implantable portion 2. To recharge a rechargeable cell contained within the implantable portion 2, an external charging head 9 connected to a battery charging unit 11 is included. The need for the charging head 9 and battery charging unit 11 can be obviated by the inclusion in the implantable portion 2 of a power supply (such as a lithium cell) which is of sufficient lifetime to negate the need for recharging. The medication programming unit 3 outputs to a paper printer 13 which provides hard, readable output that can be readily interpreted by a physician.

Figure 2:
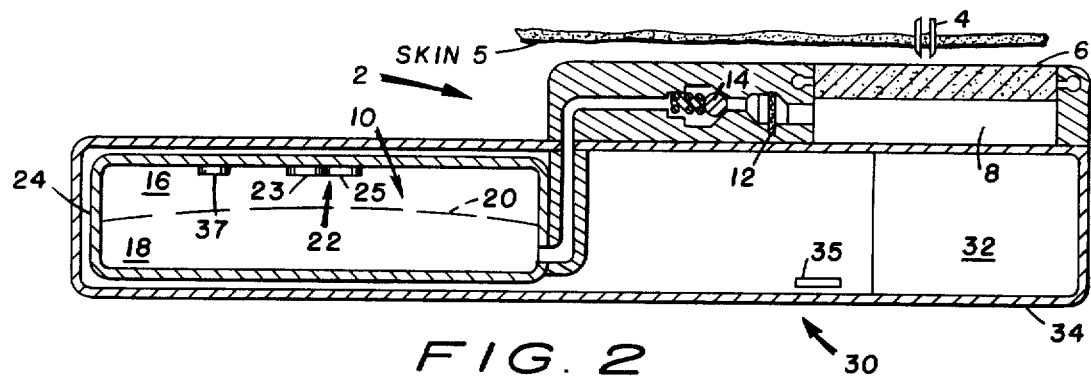
FIGS. 2 and 3 show a front cross-sectional and top view, respectively, of the implantable portion of the present medication infusion system.
Figure 3:
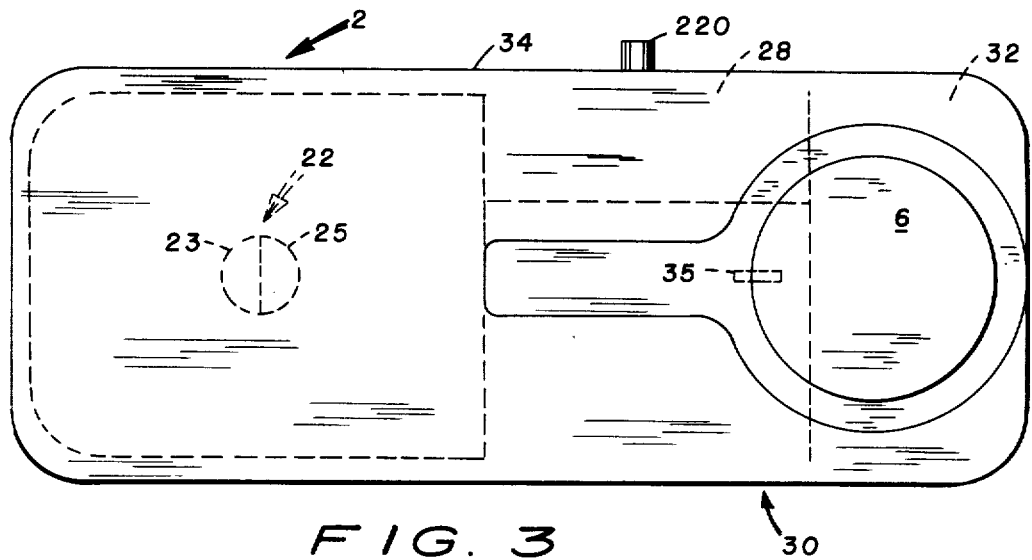

Referring now to FIGS. 2 and 3, the implantable portion 2 of an implantable programmable medication infusion system is shown. Medication is provided to the implantable portion 2 by means of a double hypodermic syringe 4 which penetrates the skin 5 and a self-sealing rubber septum 6 which covers an antechamber 8 in leak-proof fashion. Medication is introduced into the antechamber 8 through syringe 4 under pressure the level of which is controllable externally. A reservoir chamber 10, in which the medication is stored under relatively constant pressure, is fed from the antechamber 8 via a ceramic filter 12 and an inlet pressure valve 14 which permits flow only from the antechamber 8 into the reservoir chamber 10 when the pressure differential between them exceeds a predetermined threshold.

The inlet ceramic filter 12 performs various functions. Besides filtering contaminants from medication being fed into the reservoir chamber 10, the ceramic filter 12 serves to limit the rate of medication flow from the antechamber 8 into the reservoir chamber 10 or, conversely, from the reservoir chamber 10 into antechamber 8 should the inlet pressure valve 14 leak or malfunction. Further, should the self-sealing rubber septum 6 leak, the ceramic filter 12 together with the inlet pressure valve 14 prevents the inflow of body fluids into the reservoir chamber 10. Further, should the inlet pressure valve 14 and the septum 6 both leak or otherwise malfunction, the inlet ceramic filter 12 would permit only a slow flow of body fluids to enter the reservoir chamber 10, until body ambient pressure is achieved, at which time some medication could diffuse through the ceramic filter 12 but at a rate that would not be hazardous to a typical patient in which the system would be implanted.

The reservoir chamber 10 comprises a liquid-vapor portion 16 which rests atop a reservoir of medication 18, the liquid vapor portion 16 and the reservoir 18 being separated by a flexible diaphragm 20. The flexible diaphragm 20 could comprise an elastomer, a moveable bellows, or other substitutive flexible diaphragm means which would seprate the medication reservoir 18 from the liquid vapor portion 16. The liquid-vapor volume in the vapor portion 16 preferably comprises a saturated vapor in equilibrium with a small amount of Freon 113 liquid. Over normal body temperatures, Freon 113 has a linear pressure characteristic ranging from −4 psig (at 98°) to approximately −2.5 psig (at 104° F.). Using Freon 113, the medication reservoir 18 will be maintained at a pressure below that of the human body pressure up to altitudes of 8500 feet. For patients who may live above that altitude, other fluorcarbons at lower pressure may be employed. In this way, should both the septum 6 and the inlet pressure valve 14 leak, the effect would be to cause body fluids to diffuse slowly, via the inlet ceramic filter 12, into the medication reservoir 18 rather than to have a rapid flow of medication enter into the body where it could cause harm to the patient. Because of the pressure differential between the body and the medication reservoir 18, medication will not flow from the reservoir 18 into the body. As the amount of medication in the medication reservoir 18 varies, the flexible diaphragm 20 moves up or down, with the Freon 113 being converted either from liquid to vapor or vapor to liquid to provide an essentially constant pressure which will always be below one atmosphere and below normal body pressure. A reservoir chamber having a volume of approximately 10 cc would be sufficient for most applications. This amount of concentrated medication, insulin for example, could be fatal if injected over a short time. The volume of the antechamber 8 is less than 10% the size of the reservoir chamber 10. In the worst case of leakage if medication leaked from the reservoir chamber 10 into the antechamber 8 and even if the antechamber 8 leaked as well, only diluted medication would enter the body gradually passing from an area of low pressure to one of higher pressure. There is thus little likelihood of the dose being fatal. As readily seen in FIG. 2, decreasing or expanding the size of the reservoir chamber 10 would be a simple modification because of the arrangement of elements in the system. Included in the reservoir chamber 10 is a dual pressure switch 22 which can comprise a reservoir fill switch 23 for indicating when the pressure in the reservoir chamber 10 reaches a predetermined level such as −2 psig and a second switch 25 for indicating when the pressure reaches −1 psig. Fill switch 23 is used during the filling procedure to indicate (by a telemetry system to be described later) when the level of medication in the reservoir chamber 10 has reached a specific value. Should body fluids leak into the medication reservoir 18 for any reason, an increase in pressure would result that would activate the second pressure switch 25. For example, when body fluids entering reservoir 18 reach a pressure of −1 psig, this would set off a subcutaneous electrical stimulation alarm system. By having the fill switch 23 set at a lower pressure than the body fluid leak detection pressure switch 25, the filling of the reservoir 18 can be accomplished without setting off an alarm signal.

Figure 4:
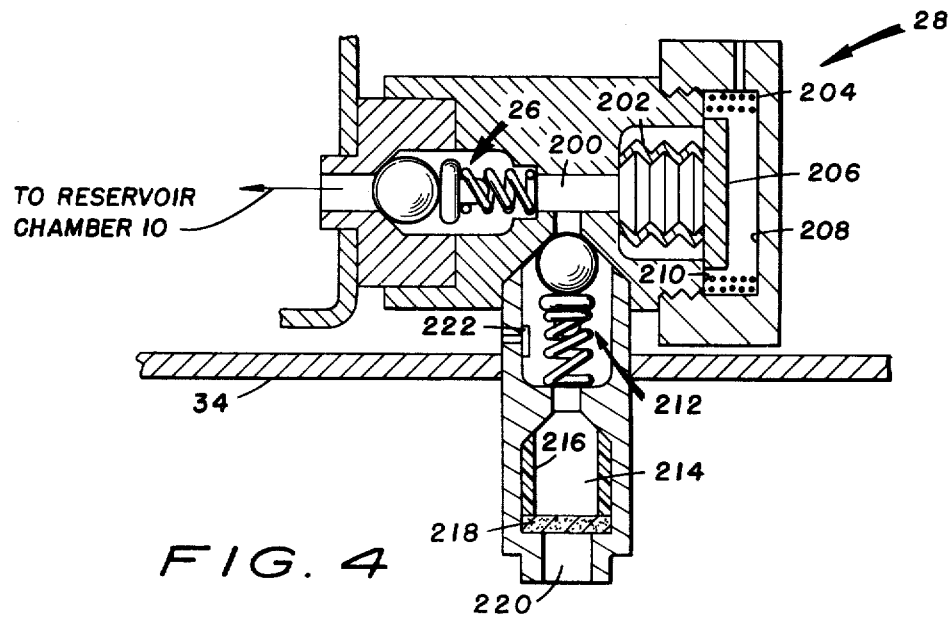
FIG. 4 shows, in detail, the mechanical construction of a pulsatile pump element of the invention.

In order to fill the reservoir chamber 10 with medication, a sequence of steps is followed. The antechamber 8 is normally filled with a saline or other innocuous solution which provides a buffer between the body and the reservoir chamber 10 and which if the septum failed would cause no harm to the patient. At the time of filling, a double hypodermic syringe 4 is directed into the antechamber 8 and saline is introduced into the antechamber 8 through one needle and exits through the other in order to flush the antechamber 8 with more saline. Once flushed, the antechamber 8 is checked for pressure integrity with saline introduced under a pressure which is less than that required to open the inlet pressure valve 14. When pressure integrity is determined, the antechamber 8 is flushed with the desired medication (such as insulin). Medication is then forced into the antechamber 8 at a pressure greater than that required to open inlet pressure valve 14. The insulin fills the medication reservoir 18 of the reservoir chamber 10 until the flexible membrane 20 contacts the dual pressure switch 22, forcing the reservoir fill switch 23, to generate a signal (e.g., at −2 psig) which indicates that the filling has been completed. The amount of medication required to fill the medication reservoir 18 is noted and then the antechamber 8 is flushed once again with innocuous saline solution. The entire reservoir chamber 10 is surrounded by a wall 24 and is isolated from the other elements of the system by means of the inlet pressure valve 14 and an interface pressure valve 26 which connects the reservoir to a pulsatile pump 28 which is shown in FIG. 4. The remaining elements of the implanted portion 2 are also shown in FIG. 2: an electronics section 30 with a battery subsection 32. As is readily seen in FIG. 2, a hermetically sealed enclosure 34 surrounds the reservoir chamber 10 as well as the pulsatile pump 28 (see FIG. 4) and the electronics section 30 which the battery subsection 32. To provide an enhanced safety feature, a fluid detector 35 is provided between the wall 24 and the hermetically sealed enclosure 34. Should either the outer hermetic enclosure 34 leak or should the reservoir chamber 10 leak, the fluid detector 35 is placed at a location where the leaking body fluids or medication would be detected. The fluid detector 35 could be a very high resistance resistor (e.g. 10 megohms) whose resistance drops significantly in the presence of fluids. A malfunction signal to warn the patient if such a leak is detected, is provided. Similarly a medication leakage detector 37 in the liquid-vapor volume 16 would indicate when medication was leaking into that chamber 16. This detector may also be a resistor whose value will be significantly altered by the presence of the medication. The medication leakage detector 37 when actuated would set off a distinct subcutaneous electrical stimulation alarm signal that can be detected by the patient.

FIG. 4 illustrates the pulsatile pump 28 shown in the top view of the implanted portion 2 shown in FIG. 3.

The interface pressure valve 26 shows where medication enters the pulsatile pump 28 when the differential in pressure between the reservoir chamber 10 and a medication storing means 200 (inside the pulsatile pump 28) reaches a level sufficient to open the inlet pressure valve 26. In the preferred embodiment shown in FIG. 4, this differential in pressure is caused by the expansion of a spring bellows 202 in response to an electrical pulse introduced to a pulsing coil 204 which surrounds a plate 206 which is attached to the spring bellows 202. When a pulse passes through the pulsing coil 204, plate 206 is driven to a forward stop 208. This action of expanding the storing means 200 causes the interface pressure valve 26 to open, thereby allowing medication from the reservoir chamber 10 to fill the medication storing means 200. The plate 206 is a permanent magnet (or, possibly, a magnetizable material) which moves in response to a current induced magnetic force. When current in the pulsing coil 204 ceases, the spring force of the bellows 202 returns the plate 206 to a position against a backstop member 210. The amount of travel of plate 206 is thus fixed, rendering the stroke volume of the pulsatile pump 28 constant and independent of the electrical pulse current or pulse width into the pulsing coil 204 as long as certain minimum currents and pulse width is provided. The maximum pressure that can be exerted by the pulsatile pump 28 is dependent on the spring force that can be exerted by the bellows 202 as well as the cross sectional area of plate 206 which is in contact with the medication in the storing means 200. More simply, $p_{max} = F/A$, where $p_{max}$ is the maximum pressure that can be created by the spring force of the bellows within the medication storing means 200, F is the spring force of bellows 202, and A is the portion of surface area of plate 206 which is in contact with the medication in the medication storing means 200 which extends into the bellows 202. Should a malfunction occur in the electronics and a continuous sequence of rapid pulses be introduced to the pulsing coil 204, causing the plate 206 to reciprocate, the return of the plate 206 to its original position against the backstop member 210 would be inhibited once the pressure in the storing means 200 exceeded $p_{max}$. The pressure builds up rapidly because of the output flow resistance caused by the ceramic filter 218. The possibility of introducing drugs or other medication at an unsafe high pressure or high rate is thus essentially eliminated.

An outlet pressure valve 212 connects the storing means 200 in the pulsatile pump 208 with an outlet chamber 214. In operation, when the plate 206 returns toward its original position against backstop 210 after being reciprocated by the action of the pulsing coil 204 and the bellows 202, an increase in pressure in the storing means 200 results. When the pressure differential between the pressure in the storing means 200 and the pressure in outlet chamber 214 exceeds that required to open outlet pressure valve 212, medication flows into outlet chamber 214 from the medication storing means 200. To prevent large spurts or pulses of medication from entering the body over a short period of time, an elastic wall 216 and an output ceramic filter 218 are provided at the entrance to the outlet 220 of outlet chamber 214. The output ceramic filter 218 serves to resist the flow of medication from the outlet chamber 214 into the living body. The elastic wall 216 acts as a type of capacitance to flow, deforming when a pulse of medication is fed into the outlet chamber 214, the elastic wall 216 thus serving as a fluid accumulator. The combination of the elastic wall 216 and the output ceramic filter 218 comprises a fluid or mechanical RC network that provides medication into the body within an initial rise followed by a decaying flow. The time constant which is fairly long, is determined by the elasticity of the elastic wall 216 and the resistance of the output ceramic filter 218. In addition, the output ceramic filter 218 disallows medication from being diffused into the body at a high rate, should both the interface pressure valve 26 and the outlet pressure valve 212 fail to seal.

Should valve 212 leak, there would be a slow diffusion of medication through the ceramic filter 218 until the pressure in the storing means 200 is essentially equal to ambient body pressure. However, since the volume means 200 is very small and since the medication fluid is essentially incompressible, very little medication can diffuse out and that amount only at a slow rate. Should both valves 26 and 212 weak, body fluids would then diffuse into the reservoir 18 because it is at a pressure below body ambient pressure. A rise in pressure in the medication reservoir 18 relative to that of the ambient body pressure would cause the −1 psig switch to be activated setting off an alarm. Further, the medication then could not diffuse through the outlet ceramic filter 218 at an unsafe rate, because there is no pressure differential across the flow resistance of the ceramic filter 218.

Safety of the output is best understood by considering the various pressure levels in the pulsatile pump 28. With a bellows spring force which gives a maximum pressure, $p_{max}$, of 15 psig and with an outlet pressure valve drop of 5 psi, it is possible for the pulsatile pump 28 to provide a pressure as high as 10 psig in the outlet chamber 214. The pressure in the outlet chamber 214 is significantly greater than the body ambient pressure of approximately 0 psig or the diastolic blood pressure which is approximately 2 psig. The resistance of the output ceramic filter 218 is selected to limit the drug flow to a given safe level, for example less than 50% the maximum pumping flow at which the pulsatile pump 28 is designed to operate. As with the inlet ceramic filter 12 (of FIG. 2) the outlet ceramic filter 218 also filters out contaminants moving in either direction, from the outlet chamber 214 into the body or from the body into the outlet chamber 214. Also included in the pulsatile pump 28 is a pressure transducer 222 which is shown located in the outlet chamber 214 but could be located wherever it could detect and respond to a pressure change corresponding to medication being pumped from the pump 28. The pressure transducer 222 produces an electrical output when a pressure pulse of medication enters the outlet chamber 214. The pressure transducer 222, in other words, detects the pressure pulses which are provided each time the spring bellows 202 returns the plate 206 to its original position against backstop 210. By comparing the pulsing from pulsing coil 204 with the pulsing generated by pressure transducer 222, an indication is given as to whether an absence or insufficient number of pulses or medication have been provided to the body. An indication of extra pulses of medication compared to the number of electrical pulses may also be provided.

Figure 5:
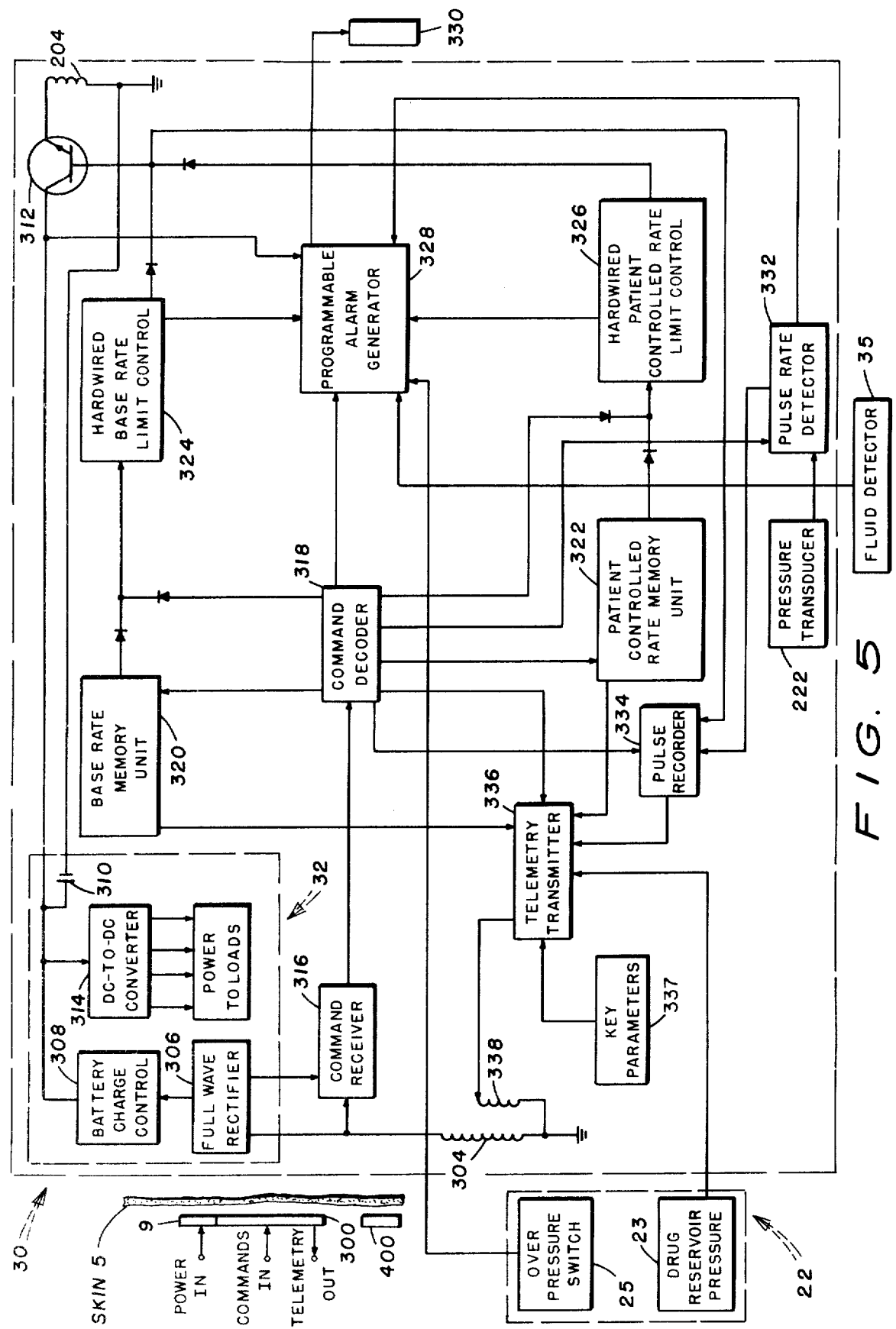
FIG. 5 is a block diagram showing the electronics of the invention.

The pulsing signal to pulsing coil 204 as well as the pulse output from the pressure transducer 222 are better understood with reference to FIG. 5 a block diagram of the electronics section 30 shown in FIGS. 2 and 3. As seen in FIG. 5, the electronics section 30 communicates with a communication head 300 which is external to the body, communicating through skin 5 by means of radio signals which includes an alternating magnetic field. The communications head 300 provides both power inputs and commands, including programmable inputs, to the electronics section 30. Power is provided by means of an alternating field, e.g. a magnetic field, which is communicated to a pickup coil 304 which is implanted together with the rest of the electronics section 30 in the body. The pickup coil 304 receives an AC power signal from communications head 300 and passes it on to a full wave rectifier 306. One rectified output from the full wave rectifier 306 enters a battery charge control 308 which provides a fixed DC charging signal to a power cell 310. The power cell 310 can be a nickel-cadmium cell which is readily rechargeable off a rectified signal at a typical frequency of 20 kHz. Alternatively, a lithium-type solid state battery can be used instead of the nickel-cadmium cell in which case the charging circuitry would be eliminated, the lithium type battery providing sufficient power over a long term, thereby obviating the need for recharging. The power cell 310 provides a biasing voltage to a transistor switch 312, the output of which enters the pulsing coil 204 previously described in the context of the pulsatile pump 28. In addition to providing power to the power cell 310, rectified power is also introduced to a DC to DC converter 314 the purpose of which is to provide power at the proper levels to the various loads in the system. In addition to the AC power signal, pick-up coil 304 also receives a train of serial digital bits from the communication head 300. The digital bits comprise commands for programmable inputs which are conveyed, via the pickup coil 304 to a command receiver 316. The signals from the command receiver 316 enter a command decoder 318 which determines if the digital bits are in a proper sequence and, if so, what action in the system the commands dictate. It should be noted that the full wave rectifier 306, the battery charge controller 308, the command receiver 316, and the command decoder 318 are powered only when an AC signal is picked up by the pickup coil 304. This, of course, prevents the possibility of detecting stray signals as commands and provides power savings. To be sure, the power savings achieved could make possible the use of the aforementioned lithium cell which would not require recharging. From the command decoder 318, programmable inputs and other commands can be provided to a number of elements. A programmable base rate is entered into a base rate memory unit 320 which stores a value indicating the number of pulses of medication which are requested to be provided to a patient during a normal preselected period of time. A second programmable input is provided a patient controlled rate memory unit 322 which stores a value indicating a number of pulses of medication that are requested to be introduced into the body over a given period of time during which the patient eats a meal or otherwise alters the chemical balance of the body (as by exercising). Associated with the base rate memory unit 320 is a hardwired base rate limit control 324 which sets a maximum rate that can override requests of the base rate memory unit 320 which are excessive. Similarly, a hardwired patient controlled rate limit control 326 provides a fixed maximum number of pulses which can be provided at a time after a meal or at other times and under other conditions. As long as the base rate and patient controlled rate values stored in memory units 320 and 322 respectively, do not exceed the hardwired values fixed within limit controls 324 and 326, respectively, an output pulse is provided to the input of transistor switch 312 to stimulate a pulse output from pulsing coil 204. Should the rate of either memory unit 320 or 322 exceed the hardwired limits in the limit control elements 324 or 326 respectively, a "rate request exceeds limit" signal is fed from the limit control element 324 or 326 into a programmable alarm generator 328 which provides an electrical signal to a stimulation electrode 330 implanted subcutaneously. By the stimulation electrode 330, the patient is informed by means of a subcutaneous stimulation that one of the memory units 320 or 322 is requesting more than the maximum allowable number of pulses.

It should be noted that the signal to the stimulation electrode 330 can serve the dual function of not only providing the patient with a subcutaneous electrical stimulation but may also be the source of a signal detected by the communication head 300 communicated to the patient or his physician either or both that a failure has occurred. As shown in FIG. 5, the electrode 330 will be isolated and should be insulated from the outside of the hermetically sealed enclosure 34 of the implanted portion 2.

A particularly significant feature of the invention resides in the programmability of the alarm generator 328 based on input commands from the command decoder 318. The alarm generator 328 can be switched on or off and the voltage produced by the generator and hence the electrode 330 can be varied in response to signals emanating from the communication head 300 and channeled through the command receiver 316 to the command decoder 318. In addition, to check the proper operation of the system, the command decoder 318 can receive test signals which can simulate actual occurrences to determine whether the circuitry in the electronic section 30 is operating properly. For example, extra pulses from the command decoder 318 can be entered into the hardwired limit control elements 324 and 326. These extra pulses can be added to the pulses provided by the base rate and the patient controlled rate memory units in order to exceed the hardwired base rate and the hardwired patient-controlled rate, respectively. When the rates are exceeded, the alarm generator 328 will provide a signal. In this way, the alarm generator 328 can be used to check the operation of the limit control elements 324 and 326 and also familiarize the patient with the corresponding subcutaneous stimulation emitted by the tickle electrode 330. The programmable alarm generator 328 also receives inputs from the pressure switch 22 and the fluid detector 35 both shown in FIG. 2. If body fluids leak into the reservoir 18, the pressure switch 25 will be activated, indicating this fault condition to the patient by means of the activation of the alarm generator 328 and the electrode 330. If the patient was unconscious, voltage levels on the patient's skin at the site of the implanted portion 2 could be used by the physician to indicate if a malfunction has occurred and which malfunction it was. Further, as previously described, should fluid leak out of the reservoir chamber 10 and onto the lining of the enclosure 34 or, alternatively, if body fluid should leak in through the enclosure 34, the fluid detector 35 would sense such leakage and, as shown in FIG. 5, would provide input to the alarm generator 328. Still another input to the alarm generator 320 comes from the power cell 310 associated with transistor switch 312. The voltage level of the power cell 310 is communicated to the alarm generator 328, a tickle or subcutaneous stimulation being generated when the voltage is below a predetermined level. Finally, referring back to the pulsatile pump 28 of FIG. 4, the electrical pressure transducer 222 provides a signal which is compared to a programmed "insufficient rate" value emanating from the command decoder 318. If the number of pulses sensed by the pressure transducer 222 over a specified period of time are less than the number of pulses associated with the "insufficient rate" command input, a pulse rate detector 332 will provide an output indicating that an insufficient amount of medication is being provided to the patient over the specified time. The output of pulse rate detector 332 (FIG. 5) also enters the tickle generator 328 to provide a subcutaneous tickle detectable by the patient. It should be noted that the various mentioned failures in the system result in subcutaneous stimulations each of which may be different in stimulation magnitude, duration, or periodicity. For example, the stimulation may range between one to four volts and may vary in frequency above and below 20 pulses per second and most importantly, a variety of pulse patterns may be used each unique to a particular malfunction or warning. Additional warnings that might be used are: (1) medication has leaked into the liquid-vapor volume, (2) only 10% of the medication remains in the reservoir, (3) only 5 days medication remains.

In addition to pulsing the pump coil 204, the outputs of the limit control elements 324 and 326 also provide input to a pulse recorder 334. Pulse recorder 334 maintains a running history of how many electrical pulses have been provided to the pulsatile pump 28 since the last refill of the reservoir 18 (in FIG. 1). An "interrogate" signal from the command decoder 318 instructs the pulse recorder 334 to provide the history to a telemetry transmitter 336 which communicates the pulse history to a telemetry coil 338. The pulse recorder 334 would record both the number of pulses delivered to the pumping coil 204 and the number of pulses detected by the pressure transducer 222 and/or the difference between these two numbers. The telemetry coil 338, in turn, provides its output through radio frequency signals to a telemetry receiving antenna in the communication head 300. In addition to the pulse history the telemetry transmitter 336 also receives, during programming, inputs from the base rate memory unit 320 and patient controlled rate memory unit 322 which are transmitted back to the communication head 300 that the desired base rate and patient controlled rate, respectively, have been programmed into the corresponding memory unit 320 or 322. Similarly, other key parameters 337 of the system are also conveyed by means of the telemetry transmitter 336 back to the communication head 330. For example, the exact pressure transducer output waveform would be telemetered. Of course, the pressure waveform signal would only be transmitted when the telemetry system is powered. Similarly, the reservoir fill switch 23 placed in the reservoir chamber 10 to indicate when it has reached a predetermined fill level is also connected via the telemetry transmitter 336 and telemetry coil 338 to the communication head 300 to indicate when the reservoir 18 has been filled with medication. Finally, a simulated low battery voltage signal can be conveyed from the command decoder 318 to the telemetry transmitter 336 to check that portion of the status circuitry. As with the full wave rectifier 306, battery charge control 308, command receiver 316, and command decoder 318, the telemetry transmitter 336 is powered only during programming, interrogation, testing with simulation signals, and power cell charging.

Figure 6:
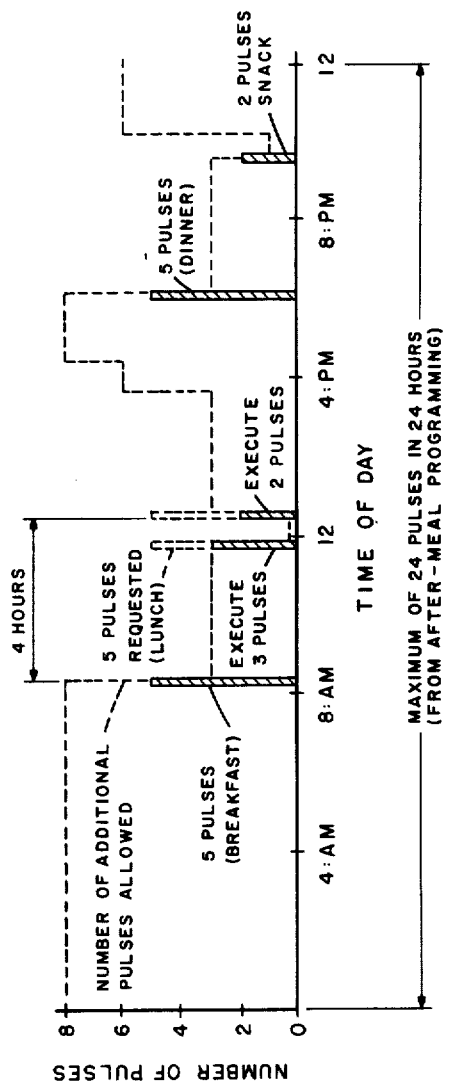
FIG. 6 shows a method of programming the rate of medication infusion into a patient by use of the maximum running integral dosage limiting technique.

Reference is now made to FIG. 6 which shows a method of programming the patient controlled memory unit 322. The significance of the method lies in the fact that it provides two maximum running integral dose limits in response to requests for medication. Two maximum integral number of pulses for two different time periods are provided. Both are independent of the time of day and therefore would be effective regardless of the patients eating or working schedule, which schedule change might be a result of the patient changing time zones. In the sample graph of FIG. 6, a maximum of eight pulses for a four hour period and twenty-four pulses for any twenty-four hour period are imposed as maximum running integral dose limits. These rate settings can, of course, be altered depending on patient needs and medication to be administered and time periods other than 4 hours or 24 hours could be used. In FIG. 6, the number of pulses is shown as a function of time.

In FIG. 6, at midnight, the number of pulses that are allowed in the 4 hour period is eight. Shortly after 8 A.M. five pulses are requested diminishing the number of additional pulses allowed to three pulses. Prior to noon, within the four hour time period, a five pulse request is entered. In accordance with the maximum running integral four hour restraint, only three pulses are permitted but the remaining two pulses in the request are stored in the memory unit 322 (FIG. 5) to be executed at the end of the four hour period beginning immediately after four hours past the delivery time for the after breakfast pulsing. Shortly after noon, when the four hours are over the two pulses are executed. It should be noted that shortly after noon the three pulses provided just before noon were subtracted from the eight pulse allowance. The dispensing of three pulses prior to noon is not eradicated until four hours thereafter, or shortly before 4 P.M. Shortly before 4 P.M. the three pulse allowance is automatically raised to six pulses, accounting for the three pulses executed just before noon. Shortly after 4 P.M., the allowance automatically rises to eight pulses thereby accounting for the two pulses executed shortly after noon. At approximately 6 P.M. the patient has dinner requiring five pulses and the allowance diminishes to three pulses. Shortly before 10 P.M. the patient has a snack which requires two pulses of medication diminishing the allowance to one pulse. At approximately 10 P.M. the five pulses provided at dinner are no longer of import and the allowance is raised by those five pulses to a six pulse level allowance. The importance of FIG. 5 is readily apparent when one considers the various time zones or work schedules a patient may go through from time to time in the course of his life. The program in FIG. 6 provides sufficient safety and flexibility for a wide variety of patients.

Figure 7:
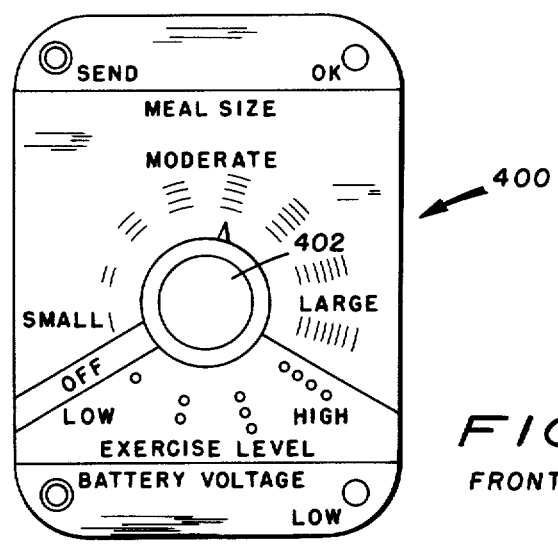
FIGS. 7 and 8 are illustrative of a patient programming unit.

Referring now to FIG. 7, the front view of a patient programming unit 400 is shown. In the center of the unit is a dial 402 which can be rotated to indicate the size of a meal eaten by the patient or the amount of exercise he has undergone, in order to provide inputs indicating the amount of medication needed. Output from the patient programming unit 400 is detected by the pickup coil 304 of FIG. 5 as commands. Whether or not the request is valid is determined in the electronic section 30 and is conveyed back to the patient programming unit 400 by telemetry. A signal by the patient programming unit 400 to the patient indicates whether his request has been satisfied. The patient programming unit 400 will be provided both with audio and visual outputs rendering it particularly useful for those patients having either visual or hearing handicaps.

Figure 8:
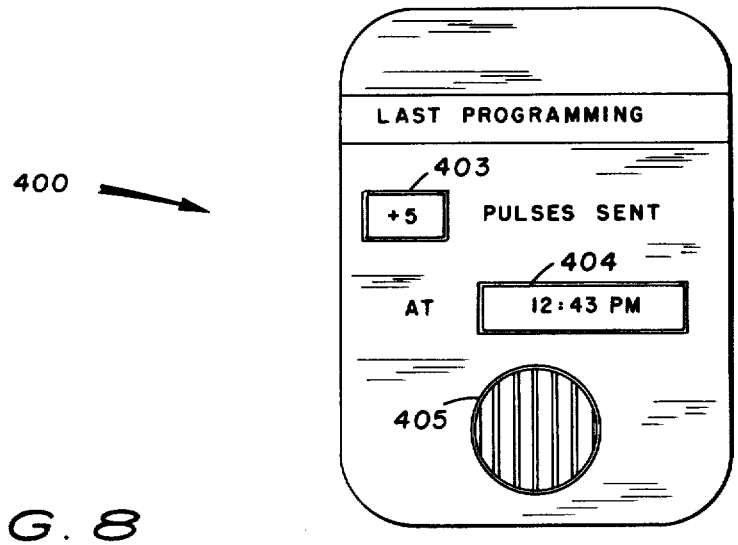

In FIG. 8 is the rear view of the patient programming unit 400. The rear side of the patient programming unit 400 will provide information indicating the number of pulses sent at the last request 403; the time of the last request 404; and possibly (but is not shown) the number of pulses which can be sent within the program restraints. By programming ROMS (not shown) in the patient programming unit 400 in accordance with the running integral programs shown in FIG. 5 and "OK" or "TOO MUCH REQUESTED" video and/or audible output can be provided. The audio output would emanate from the loudspeaker 405. When the request leads to the dispensing of a pulse or pulses of medication into the outlet chamber. A "MEDICATION SENT" signal from the implanted portion 2 is relayed to the patient programming unit 400 to actuate an audio indication by loudspeaker 405 or by visual means.

It should be understood that alternative embodiments are contemplated by the present invention. For example, the antechamber 8 can comprise a vitreous carbon insert in the skull, or other suitable, accessible place on the body, coupled with a tube directed to the reservoir chamber 10 which may be located in the torso. The filling procedure and elements of the antechamber 8 (e.g. the septum 6) would remain the same with the vitreous carbon insert. The inlet pressure valve 14 and filter 12 would still separate the insert and tube from the reservoir chamber 10. Similarly, in addition to the patient programming unit 400, a physician's unit may be provided which indicates: when the medication reservoir 18 (of FIG. 1) has been filled, the pulse history from the pulse recorder 334, and other signals from the telemetry transmitter 336 of FIG. 4. Such a physician's unit would be connected to the telemetry portion of the communication head 300.

What is claimed is:

1. A programmable infusion system for providing medication to a living body of a patient comprising:
   an infusion apparatus for implantation in said living body, said apparatus including
     a medication reservoir for storing selected medication,
     means for infusing said selected medication stored in said medication reservoir into said living body, said infusion means having at least one remotely commandable operational characteristic,
     command receiver means coupled to said infusion means for receiving command signals, and
     means for telemetering operational information pertaining to said infusion apparatus out of said living body;
   command source means external to said living body for transmitting said command signals to be received by said command receiver means; and
   means for receiving said telemetered operational information external to said living body.

2. A programmable infusion system in accordance with claim 1, wherein one of said command signals transmitted by said command source means comprises a signal which corresponds to a selected operational rate at which said infusion means will infuse said selected medication into said living body.

3. A programmable infusion system in accordance with claim 1, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of said medication dose inputs.

4. A programmable infusion system in accordance with claim 3, wherein said infusion apparatus further comprises electronic control means coupled to said infusion means and said command receiver means, said electronic control means including means for maintaining a history of the infusion rate at which said infusion means has operated, said electronic control means including means for precluding the infusion of said selected medication by said infusion means if said rate requested by said patient programming unit exceeds a predetermined safe medication infusion rate based on said maintained history.

5. A programmable infusion system in accordance with claim 4, wherein said electronic control means is coupled to said telemetry means, said patient programming unit including means for indicating to said patient if said selected infusion rate exceeds said predetermined safe medication infusion rate, said electronic control means selectively sending a signal to said indicating means via said telemetry means and said telemetry receiving means, said telemetry receiving means being coupled to said indicating means.

6. A programmable infusion system in accordance with claim 3, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

7. A programmable infusion system in accordance with claim 1, further comprising means for selectively supplying power to said command receiver means, said supply means being coupled to an external power source, said supply means being external to said living body, said infusion means being powered by an implanted power source.

8. A programmable infusion system, in accordance with claim 7, wherein said supply means provides an alternating field.

9. A programmable infusion system, in accordance with claim 8, wherein said infusion apparatus further comprises detector means for detecting said alternating field and for converting the same into electrical energy, said detecting means being coupled to said command receiver.

10. A programmable infusion system in accordance with claim 9, wherein said infusion apparatus further comprises means for rectifying said electrical energy into a d.c. power signal.

11. A programmable infusion system in accordance with claim 10, wherein said d.c. power signal is coupled to said implanted power source to effect the charging thereof.

12. A programmable infusion system in accordance with claim 10, wherein said telemetry means is coupled to said rectifier means and is powered by said d.c. power signal.

13. A programmable infusion system in accordance with claim 7, wherein said telemetry means is also supplied power by said supply means.

14. A programmable infusion system in accordance with claim 7, further comprising means for selectively recharging said implanted power source, said recharging means being powered by said supply means.

15. A programmable infusion system in accordance with claim 1, wherein said infusion means comprises a fluid handling mechanism for delivering said selected medication, said operational information including information about the operation of said fluid handling mechanism.

16. A programmable infusion system in accordance with claim 15, wherein said fluid handling mechanism comprises means for pumping said selected medication.

17. A programmable infusion system in accordance with claim 16, wherein said pump means further comprises pressure limiting means for controlling the amount of medication pumped by said pump means.

18. A programmable infusion system in accordance with claim 16, wherein said pump means operates in a pulsatile mode.

19. A programmable infusion system in accordance with claim 18, wherein said pump means pumps a fixed volume of said selected medication each time said pump means is pulsed.

20. A programmable infusion system in accordance with claim 16, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means.

21. A programmable infusion system in accordance with claim 20, wherein said variable volume means comprises at least one flexible wall, movement of said at least one flexible wall varying the volume of said variable volume means, and means for moving said at least one flexible wall.

22. A programmable infusion system in accordance with claim 21, further comprising spring means for urging said at least one flexible wall in a manner which decreases the volume of said variable volume means, the magnitude of the force applied to and stored by said spring means increasing as the volume of said variable volume means increases due to the displacement of said at least one flexible wall thereof by said moving means.

23. A programmable infusion system in accordance with claim 22, wherein said at least one flexible wall comprises a bellows assembly having mounted on one end thereof a plate, the other end of said bellows assembly being in communication with said selected medication, the walls of said bellows assembly serving as said spring means.

24. A programmable infusion system in accordance with claim 23, wherein said plate has a surface in contact with said selected medication when drawn into said variable volume means.

25. A programmable infusion system in accordance with claim 24, wherein said bellows assembly is inhibited from moving said plate when the pressure (p) in said variable volume means exceeds the spring force (F) of said bellows assembly divided by the wetted area (A) of said surface of said plate in contact with said selected medication, that is when $p > F/A$.

26. A programmable infusion system in accordance with claim 23, wherein said plate is magnetizable, said moving means comprising a coil disposed proximate to said plate, said coil selectively radiating a pulsing magnetic field, pulsing of said coil causing said plate to be moved.

27. A programmable infusion system in accordance with claim 26, wherein said plate comprises a permanent magnet.

28. A programmable infusion system in accordance with claim 23, further comprising means for limiting the distance said plate can move in both a volume increasing direction and a volume decreasing direction.

29. A programmable infusion system in accordance with claim 20, wherein said infusion means further comprises:
an interface pressure value through which said selected medication enters said variable volume means from said medication reservoir, said interface pressure valve being normally closed;
an outlet chamber which is in communication with said living body; and
an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure pulse.

30. A programmable infusion system in accordance with claim 29, wherein said outlet chamber comprises an elastic wall having a fluidic capacitive effect on the flow of said selected medication and a filter element through which liquid flow to the said living body is resisted, said elastic wall and said filter comprising a fluid resistance-capacitance arrangement with respect to said flow of said selected medication from said outlet chamber into said living body.

31. A programmable infusion system in accordance with claim 19, further comprising means for feeding said selected medication into said living body from said pump means in a flow which decays exponentially over time.

32. A programmable infusion system in accordance with claim 31, wherein said feeding means comprises a mechanical resistance (R) and a mechanical capacitance (C) circuit resulting in an exponentially decaying outflow of medication for each said fixed volume pulse.

33. A programmable infusion system in accordance with claim 20, wherein said infusion means further comprises an outlet chamber which is in communication with said living body, said pump means expelling said selected medication into said outlet chamber, and means for monitoring the operation of said pump means, said monitoring means being disposed in said outlet chamber and providing a signal in response to a pressure pulse in said outlet chamber caused by said pump means, said monitoring means being operably coupled to said telemetry means.

34. A programmable infusion system in accordance with claim 33, wherein said monitoring means comprises a pressure transducer.

35. A programmable infusion system in accordance with claim 33, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

36. A programmable infusion system in accordance with claim 35, further comprising second means for indicating the operation of said pump means when a signal is provided by said monitoring means absent a decrease in volume of said variable volume means, said second indicating means being operably coupled to said telemetry means.

37. A programmable infusion system in accordance with claim 16, further comprising means for monitoring the operation of said pump means, said monitoring means being operably coupled to said telemetry means.

38. A programmable infusion system in accordance with claim 37, wherein said monitoring means comprises pressure sensing means disposed in the path of flow of said selected medication into said living body, said pressure sensing means providing a signal in response to a pressure pulse in said path of flow.

39. A programmable infusion system in accordance with claim 38, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

40. A programmable infusion system in accordance with claim 39, further comprising second means for indicating the operation of said pump means when a signal is provided by said monitoring means absent a decrease in volume of said variable volume means, said second indicating means being operably coupled to said telemetry means.

41. A programmable infusion system in accordance with claim 1, wherein one of said at least one remotely commandable operational characteristic comprises an infusion rate variable on command, said infusion apparatus further comprising means for inhibiting said infusion means from infusing said selected medication if a preselected medication infusion rate is exceeded by a commanded infusion rate, said inhibiting means being operably coupled to said infusion means.

42. A programmable infusion system in accordance with claim 41, wherein said inhibiting means comprises at least one means for defining a fixed infusion rate limit.

43. A programmable infusion system in accordance with claim 42, wherein said at least one means for defining a fixed infusion rate limit is hardwired.

44. A programmable infusion system in accordance with claim 41, wherein said preselected medication infusion rate is remotely selectable.

45. A programmable infusion system in accordance with claim 41, wherein said preselected medication infusion rate comprises a remotely selectable rate and a fixed rate, said remotely selectable rate being limited by said fixed rate.

46. A programmable infusion system in accordance with claim 45, wherein said inhibiting means comprises:
at least one programmable rate memory unit coupled to said command receiver means, each of said at least one programmable rate memory units for receiving and storing an infusion rate input command corresponding to said remotely selectable rate;
at least one limit control unit, each of said at least one limit control units providing a fixed rate limit; and
means for comparing each of said infusion rate input commands to a corresponding said fixed rate limit, infusion of said medication at a rate exceeding said fixed rate limit being inhibited.

47. A programmable infusion system in accordance with claim 46, further comprising command decoder means for coupling each of said at least one programmable rate memory units to said command receiver means, said command decoder means for decoding said command signals received by said command receiver means into said infusion rate inputs for receipt by and storage corresponding said at least one programmable rate memory units.

48. A programmable infusion system in accordance with claim 46, wherein each of said at least one limit control units is hardwired.

49. A programmable infusion system in accordance with claim 46, further comprising means for generating an alarm signal when any infusion rate input command exceeds a corresponding fixed rate limit.

50. A programmable infusion system in accordance with claim 46, wherein said inhibiting means precludes infusion of said medication by said infusion means when the selected said commandable infusion rate exceeds said preselected medication infusion rate during a window of time of a predetermined length which shifts continuously.

51. A programmable infusion system in accordance with claim 41, wherein said inhibiting means precludes infusion of said medication by said infusion means when the selected said commandable infusion rate exceeds said preselected medication infusion rate during a window of time of a predetermined length which shifts continuously.

52. A programmable infusion system in accordance with claim 41, wherein said infusion means includes a pump means which executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

53. A programmable infusion system in accordance with claim 52, wherein said memory rate unit also records the number of pulses which have been inhibited and causes said pump means of said infusion means to execute said pulses when said pulses can be subtracted as a result of the elapse of time from said dose limit number stored in said programmable memory rate unit.

54. A programmable infusion system in accordance with claim 52, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

55. A programmable infusion system in accordance with claim 54, wherein said rate memory unit also records the number of pulses which have been inhibited and causes said pump means of said infusion means to execute said pulses when said pulses can be subtracted from both said dose limit numbers stored in said programmable memory rate unit.

56. A programmable infusion system in accordance with claim 55, wherein said inhibiting means further comprises at least one fixed infusion rate limit which limits the total maximum infusion rate of said infusion means.

57. A programmable infusion system in accordance with claim 56, wherein said fixed infusion rate limit is hardwired.

58. A programmable infusion system in accordance with claim 54, further comprising means for generating an alarm signal when any commanded infusion rate results in the inhibiting of pulsing of said pump means by said inhibiting means.

59. A programmable infusion system in accordance with claim 58, wherein said alarm signal comprises a subcutaneous electrical stimulation.

60. A programmable infusion system in accordance with claim 54, further comprising command decoder means for coupling said command receiver means to said programmable memory rate unit, said command decoder means for decoding said command signals received by said command receiver means into said first and second maximum numbers of infusion pulses.

61. A programmable infusion system in accordance with claim 41, wherein said inhibiting means is operably coupled to said telemetry means, said inhibiting means providing a signal to said telemetry means for telemetering to said telemetry receiving means operational information pertaining to the functions of said inhibiting means.

62. A programmable infusion system in accordance with claim 41, further comprising means for generating an alarm signal when said inhibiting means inhibits said infusion means.

63. A programmable infusion system in accordance with claim 41, further comprising means for recording when said inhibiting means inhibits said infusion means.

64. A programmable infusion system in accordance with claim 63, wherein said recording means is coupled to said telemetry means, said recording means providing a signal to said telemetry means for telemetering to said telemetry receiving means operational information pertaining to said inhibiting means as recorded by said recording means.

65. A programmable infusion system in accordance with claim 1, said infusion apparatus further comprising means for generating a distinctive alarm signal pattern for each of a plurality of improper operational conditions.

66. A programmable infusion system in accordance with claim 65, further comprising means for delivering said alarm signal pattern to said living body subcutaneously.

67. A programmable infusion system in accordance with claim 66, further comprising means for detecting a medication leak, said medication detecting means being coupled to said alarm generating means, wherein one of said improper operational conditions comprises a medication leak out of said medication reservoir.

68. A programmable infusion system in accordance with claim 66, further comprising means for detecting a body fluid leak, said body fluid detecting means being coupled to said alarm generating means, wherein one of said improper operational conditions comprises a leak of body fluids into said infusion apparatus.

69. A programmable infusion system in accordance with claim 66, further comprising means for detecting the rate at which said infusion means is operating, said rate detecting means being coupled at said alarm generating mean, wherein one of said improper operational conditions comprises operation of said infusion means at an improper rate.

70. A programmable infusion system in accordance with claim 66, wherein one of said improper operational conditions comprises receiving of a command by said command receiver means which cannot be executed.

71. A programmable infusion system in accordance with claim 66, further comprising battery means for powering said infusion means and means for determining the voltage of said battery means, said voltage determining means being coupled to said alarm generating means, wherein one of said improper operational conditions comprises low battery means voltage.

72. A programmable infusion system in accordance with claim 66, further comprising means for detecting the amount of medication disposed in said reservoir, said medication amount detecting means being coupled to said alarm generating means, wherein one of said improper operational conditions comprises a preselected amount of medication remaining in said medication reservoir.

73. A programmable infusion system in accordance with claim 65, further comprising means for detecting a medication leak, said medication detecting means being coupled to said alarm means, wherein one of said improper operational conditions comprises a medication leak out of said medication reservoir.

74. A programmable infusion system in accordance with claim 65, further comprising means for detecting a body fluid leak, said body fluid detecting means being coupled to said alarm generating means, wherein one of said improper operational conditions comprises a leak of body fluids into said infusion apparatus.

75. A programmable infusion system in accordance with claim 65 further comprising means for detecting the rate at which said infusion means is operating, said rate detecting means being coupled to said alarm generating means, wherein one of said improper operational conditions comprises operation of said infusion means at an improper rate.

76. A programmable infusion system in accordance with claim 65, wherein one of said improper operational conditions comprises receiving of a command by said command receiver means which cannot be executed.

77. A programmable infusion system in accordance with claim 65, further comprising battery means for powering said infusion means and means for determining the voltage of said battery means, said voltage detecting means being coupled to said alarm generating means wherein one of said improper operational conditions comprises low battery means voltage.

78. A programmable infusion system in accordance with claim 65, further comprising means for detecting the amount of medication disposed in said reservoir, said medication amount detecting means being coupled to said alarm generating means, wherein one of said improper operational conditions comprises a preselected amount of medication remaining in said medication reservoir.

79. A programmable infusion system in accordance with claim 65, further comprising means for simulating said improper operational conditions for test purposes.

80. A programmable infusion system in accordance with claim 1, wherein said infusion means includes means for pumping a preselected amount of medication into said living body, said infusion apparatus further comprising means for recording the rate at which pumping is effected by said pump means.

81. A programmable infusion system in accordance with claim 80, wherein said recording means comprises:
means for storing the rate at which said pump means pumps over a preselected time period;
means for storing a programmable input corresponding to a minimum medication infusion rate; and
means for comparing the rate recorded by said first recited storing means to the rate stored in said second recited storing means.

82. A programmable infusion system in accordance with claim 81, further comprising means for providing an alarm signal when said rate recorded by said first recited storing means is less than said programmable input corresponding to said minimum medication infusion rate recorded by said second recited storing means.

83. A programmable infusion system in accordance with claim 81, wherein said recording means is coupled to said telemetry means for telemetering information recorded by said recording means out of said living body.

84. A programmable infusion system in accordance with claim 80, wherein said recording means comprises:
means for storing the rate at which said pump means pumps over a preselected time period; and
means for storing the rate at which said pump means is signalled to pump over said preselected time period.

85. A programmable infusion system in accordance with claim 84, further comprising means for comparing the rates recorded by both said storing means.

86. A programmable infusion system in accordance with claim 85, wherein said comparing means is coupled to said telemetry means for telemetering information outputted by said comparing means out of said living body.

87. A programmable infusion system in accordance with claim 85, further comprising means for providing an alarm signal when the rate at which said pump means pumps is different than the rate at which said pump means is signalled to pump.

88. A programmable infusion system in accordance with claim 84, wherein said recording means is coupled to said telemetry means for telemetering information recorded by said recording means out of said living body.

89. A programmable infusion system in accordance with claim 80, wherein said pump means executes in pulses, said recording means comprising a pulse rate detector comprising:
means for counting the number of times said pump means pumps over a preselected time period, said counting means storing the count;
minimum rate memory means for storing a programmable number input corresponding to a minimum medication infusion rate; and
means for comparing the number counted by said counting means with said programmable number input stored in said minimum rate memory means.

90. A programmable infusion system in accordance with claim 89, further comprising means for providing an alarm signal when said count is less than said programmable number input stored in said minimum rate memory means.

91. A programmable infusion system in accordance with claim 90, wherein said alarm signal comprises a subcutaneous electrical stimulation.

92. A programmable infusion system in accordance with claim 90, wherein said counting means comprises a pressure transducer.

93. A programmable infusion system in accordance with claim 89, wherein said comparing means is coupled to said telemetry means for telemetering information outputted by said comparing means out of said living body.

94. A programmable infusion system in accordance with claim 80, wherein said pump means executes in pulses, said recording means comprising a pulse recorder comprising:
means for counting the number of times said pump means pumps over a preselected time period, said counting means storing the count; and
means for counting the number of times said pump means is commanded to pump over said preselected time period.

95. A programmable infusion system in accordance with claim 94, wherein said pulse recorder further comprises means for comparing the numbers recorded by both said counting means.

96. A programmable infusion system in accordance with claim 95, wherein said comparing means is coupled to said telemetry means for telemetering information outputted by said comparing means out of said living body.

97. A programmable infusion system in accordance with claim 94, further comprising means for providing an alarm signal when said numbers recorded by both said counting means are different.

98. A programmable infusion system in accordance with claim 97, wherein said alarm signal comprises a subcutaneous electrical stimulation.

99. A programmable infusion system in accordance with claim 94, wherein said recording means is coupled to said telemetry means for telemetering information recorded by both said counting means out of said living body.

100. A programmable infusion system in accordance with claim 94, wherein said first recited counting means comprises a pressure transducer.

101. A programmable infusion system in accordance with claim 1, further comprising means for maintaining the pressure within said medication reservoir at a pressure level below the internal pressure of said living body.

102. A programmable infusion system in accordance with claim 101, wherein said pressure maintaining means comprises:
- a flexible diaphragm which divides said medication reservoir into a medication chamber and a liquid-vapor pool chamber; and
- a liquid vapor pool disposed within said liquid-vapor pool chamber, the proportion of liquid to vapor in said liquid-vapor pool varying in response to variations in the amount of said selected medication disposed in said medication chamber.

103. A programmable infusion system in accordance with claim 102, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetry receiving means.

104. A programmable infusion system in accordance with claim 103, wherein said switch means is activated by pressure exerted thereon by said flexible diaphragm, said pressure being less than the ambient pressure of said body.

105. A programmable infusion system in accordance with claim 102, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in said medication chamber by more than a predetermined differential.

106. A programmable infusion system in accordance with claim 105, wherein the volume of said antechamber is less than 10% the volume of said medication chamber.

107. A programmable infusion system in accordance with claim 105, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

108. A programmable infusion system in accordance with claim 1, further comprising means for programmed pumping of fixed-volume pulses of medication into said living body.

109. A programmable infusion system in accordance with claim 1, further comprising means for injecting medication into said medication reservoir, said injecting means being coupled to said telemetering receiver means, and programming means coupled to said telemetry means for indicating when ejection of medication into said medication reservoir is appropriate.

110. A programmable infusion system for providing medication to a living body of a patient comprising:
- an infusion apparatus for implantation in said living body, said apparatus including
  - a medication reservoir for storing selected medication,
  - means for infusion said selected medication stored in said medication reservoir into said living body, said infusion means having at least one remotely commandable operational characteristic and being powered by an implanted power source,
  - command receiver means coupled to said infusion means for receiving command signals, said command receiver means being powered by a power source external to said living body, and
  - means for telemetering operational information pertaining to said infusion apparatus out of said living body;
- command source means external to said living body for transmitting said command signal to be received by said command receiver means;
- means for receiving said telemetered operational information external to said living body; and
- means for selectively supplying power to said command receiver means, said supply means being coupled to said external power source, said supply means being external to said living body.

111. A programmable infusion system in accordance with claim 110, wherein said supply means provides an alternating field.

112. A programmable infusion system in accordance with claim 111, wherein said infusion apparatus further comprises detector means for detecting said alternating field and for converting the same into electrical energy, said detecting means being coupled to said command receiver.

113. A programmable infusion system in accordance with claim 112, wherein said infusion apparatus further comprises means for rectifying said electrical energy into a d.c. power signal.

114. A progammable infusion system in accordance with claim 113, wherein said d.c. power signal is coupled to said implanted power source to effect the charging thereof.

115. A programmable infusion system in accordance with claim 113, wherein said telemetry means is coupled to said rectifier means and is powered by said d.c. power signal.

116. A programmable infusion system in accordance with claim 110, wherein said telemetry means is also supplied power by said supply means.

117. A programmable infusion system in accordance with claim 110, further comprising means for selectively recharging said implanted power source, said recharging means being powered by said supply means.

118. A programmable infusion system in accordance with claim 110, wherein one of said command signals transmitted by said command source means comprises a signal which corresponds to a selected operational rate at which said infusion means will infuse said selected medication into said living body.

119. A programmable infusion system in accordance with claim 110, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of of said medication dose inputs.

120. A programmable infusion system in accordance with claim 119, wherein said infusion apparatus further comprises electronic control means coupled to said infusion means and said command receiver means, said electronic control means including means for maintaining a history of the infusion rate at which said infusion means has operated, said electronic control means including means for precluding the infusion of said selected medication of said infusion means if said rate requested by said patient programming unit exceeds a predetermined safe medication infusion rate based on said maintained history.

121. A programmable infusion system in accordance with claim 120, wherein said electronic control means is coupled to said telemetry means, said patient programming unit including means for indicating to said patient if said selected infusion rate exceeds said predetermined safe medication infusion rate, said electronic control means selectively sending a signal to said indicating means via said telemetry means and said telemetry receiving means, said telemetry receiving means being coupled to said indicating means.

122. A programmable infusion system in accordance with claim 119, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

123. A programmable infusion system in accordance with claim 110, wherein said infusion means comprises a fluid handling mechanism for delivering said selected medication, said operational information including information about the operation of said fluid handling mechanism.

124. A programmable infusion system in accordance with claim 123, wherein said fluid handling mechanism comprises means for pumping said selected medication.

125. A programmable infusion system in accordance with claim 124, wherein said pump means further comprises pressure limiting means for controlling the amount of medication pumped by said pump means.

126. A programmable infusion system in accordance with claim 124, wherein said pump means operates in a pulsatile mode.

127. A programmable infusion system in accordance with claim 126, wherein said pump means pumps a fixed volume of said selected medication each time said pump means is pulsed.

128. A programmable infusion system in accordance with claim 124 wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means.

129. A programmable infusion system in accordance with claim 128, wherein said variable volume means comprises at least one flexible wall, movement of said at least one flexible wall varying the volume of said variable volume means, and means for moving said at least one flexible wall.

130. A programmable infusion system in accordance with claim 129, further comprising spring means for urging said at least one wall in a manner which decreases the volume of said variable volume means, the magnitude of the force applied to and stored by said spring means increasing as the volume of said variable volume means increases due to the displacement of said at least one flexible wall thereof by said moving means.

131. A programmable infusion system in accordance with claim 130, wherein said at least one flexible wall comprises a bellows assembly having mounted on one end thereof a plate, the other end of said bellows assembly being in communication with said selected medication, the walls of said bellows assembly serving as said spring means.

132. A programmable infusion system in accordance with claim 137, wherein said plate has a surface in contact with a said selected medication when drawn into said variable volume means.

133. A programmable infusion system in accordance with claim 132, wherein said bellows assembly is inhibited from moving said plate when the pressure (p) in said variable volume means exceeds the spring force (F) of said bellows assembly divided by the wetted area (A) of said surface of said plate in contact with said selected medication, that is when $p > F/A$.

134. A programmable infusion system in accordance with claim 131, wherein said plate is magnetizable, said moving means comprising a coil disposed proximate to said plate, said coil selectively radiating a pulsing magnetic field, pushing of said coil causing said plate to be moved.

135. A programmable infusion system in accordance with claim 134, wherein said plate comprises a permanent magnet.

136. A programmable infusion system in accordance with claim 131, further comprising means for limiting the distance said plate can move in both a volume increasing direction and a volume decreasing direction.

137. A programmable infusion system in accordance with claim 128, wherein said infusion means further comprises:
an interface pressure valve through which said selected medication enters said variable volume means from said medication reservoir, said interface pressure valve being normally closed;
an outlet chamber which is in communication with said living body; and
an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure plate.

138. A programmable infusion system in accordance with claim 137, wherein said outlet chamber comprises an elastic wall having a fluidic capacitive effect on the flow of said selected medication and a filter element through which liquid flow to the said living body is resisted, said elastic wall and said filter comprising a fluid resistance-capacitance arrangement with respect to said flow of said selected medication from said outlet chamber into said living body.

139. A programmable infusion system in accordance with claim 127, further comprising means for feeding said selected medication into said living body from said pump means in a flow which decays exponentially over time.

140. A programmable infusion system in accordance with claim 139, wherein said feeding means comprises a mechanical resistance (R) and a mechanical capacitance (C) circuit resulting in an exponentially decaying outflow of medication for each said fixed volume phase.

141. A programmable infusion system in accordance with claim 124, wherein said infusion means further comprises an outlet chamber which is in communication with said living body, said pump means expelling said selected medication into said outlet chamber, and means for monitoring the operation of said pump means, said monitoring means being disposed in said outlet chamber and providing a signal in response to a pressure pulse in said outlet chamber caused by said pump means, said monitoring means being operably coupled to said telemetry means.

142. A programmable infusion system in accordance with claim 141, wherein said monitoring means comprises a pressure transducer.

143. A programmable infusion system in accordance with claim 141, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

144. A programmable infusion system in accordance with claim 143, further comprising second means for indicating the operation of said pump means when a signal is provided by said monitoring means absent a decrease in volume of said variable volume means, said second indicating means being operably coupled to said telemetry means.

145. A programmable infusion system in accordance with claim 124, further comprising means for monitoring the operation of said pump means, said monitoring means being operably coupled to said telemetry means.

146. A programmable infusion system in accordance with claim 145, wherein said monitoring means comprises pressure sensing means disposed in the path of flow of said selected medication into said living body, said pressure sensing means providing a signal in response to a pressure pulse in said path of flow.

147. A programmable infusion system in accordance with claim 146, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

148. A programmable infusion system in accordance with claim 147, further comprising second means for indicating the operation of said pump means when a signal is provided by said monitoring means absent a decrease in volume of said variable volume means, said second indicating means being operably coupled to said telemetry means.

149. A programmable infusion system in accordance with claim 110, wherein one of said at least one remotely commandable operational characteristic comprises an infusion rate variable on command, said infusion apparatus further comprising means for inhibiting said infusion means from infusing said selected medication if a preselected medication infusion rate is exceeded by a commanded infusion rate, said inhibiting means being operably coupled to said infusion means.

150. A programmable infusion system in accordance with claim 149, wherein said inhibiting means comprises at least one means for defining a fixed infusion rate limit.

151. A programmable infusion system in accordance with claim 150, wherein said at least one means for defining a fixed infusion rate limit is hardwired.

152. A programmable infusion system in accordance with claim 149, wherein said preselected medication infusion rate is remotely selectable.

153. A programmable infusion system in accordance with claim 149, wherein said preselected medication infusion rate comprises a remotely selectable rate and a fixed rate, said remotely selectable rate being limited by said fixed rate.

154. A programmable infusion system in accordance with claim 153, wherein said inhibiting means comprises:
  at least one programmable rate memory unit coupled to said command receiver means, each of said at least one programmable rate memory units for receiving and storing an infusion rate input command corresponding to said remotely selectable rate;
  at least one limit control unit, each of said at least one limit control units providing a fixed rate limit; and
  means for comparing each of said infusion rate input commands to a corresponding said fixed rate limit, infusion of said medication at a rate exceeding said fixed rate limit being inhibited.

155. A programmable infusion system in accordance with claim 154, further comprising command decoder means for coupling each of said at least one programmable rate memory units to said command receiver means, said command decoder means for decoding said command signals received by said command receiver means into said infusion rate inputs for receipt by and storage in corresponding said at least one programmable rate memory units.

156. A programmable infusion system in accordance with claim 154, wherein each of said at least one limit control units is hardwired.

157. A programmable infusion system in accordance with claim 154, further comprising means for generating an alarm signal when any infusion rate input command exceeds a corresponding fixed rate limit.

158. A programmable infusion system in accordance with claim 157, wherein said alarm signal comprises a subcutaneous electrical stimulation.

159. A programmable infusion system in accordance with claim 154, wherein said inhibiting means precludes infusion of said medication by said infusion means when the selected said commandable infusion rate exceeds said preselected medication infusion rate during a window of time of a predetermined length which shifts continuously.

160. A programmable infusion system in accordance with claim 149, wherein said inhibiting means precludes infusion of said medication by said infusion means when the selected said commandable infusion rate exceeds said preselected medication infusion rate during a window of time of a predetermined length which shifts continuously.

161. A programmable infusion system in accordance with claim 149, wherein said infusion means includes a pump means which executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

162. A programmable infusion system in accordance with claim 161, wherein said memory rate unit also records the number of pulses which have been inhibited and causes said pump means of said infusion means to execute said pulses when said pulses can be subtracted as a result of the elapse of time from said dose limit number stored in said programmable memory rate unit.

163. A programmable infusion system in accordance with claim 161, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

164. A programmable infusion system in accordance with claim 163, wherein said rate memory unit also records the number of pulses which have been inhibited and causes said pump means of said infusion means to execute said pulses when said pulses can be subtracted from both said dose limit numbers stored in said programmable memory rate unit.

165. A programmable infusion system in accordance with claim 164, wherein said inhibiting means further comprises at least one fixed infusion rate limit which limits the total maximum infusion rate of said infusion means.

166. A programmable infusion system in accordance with claim 165, wherein said fixed infusion rate limit is hardwired.

167. A programmable infusion system in accordance with claim 163, further comprising means for generating an alarm signal when any commanded infusion rate results in the inhibiting of pulsing of said pump means by said inhibiting means.

168. A programmable infusion system in accordance with claim 167, wherein said alarm signal comprises a subcutaneous electrical stimulation.

169. A programmable infusion system in accordance with claim 163, further comprising command decoder means for coupling said command receiver means to said programmable memory rate unit, said command decoder means for decoding said command signals received by said command receiver means into said first and second maximum numbers of infusion pulses.

170. A programmable infusion system in accordance with claim 149, wherein said inhibiting means is operably coupled to said telemetry means, said inhibiting means providing a signal to said telemetry means for telemetering to said telemetry receiving means operational information pertaining to the functions of said inhibiting means.

171. A programmable infusion system in accordance with claim 149, further comprising means for generating an alarm signal when said inhibiting means inhibits said infusion means.

172. A programmable infusion system in accordance with claim 149, further comprising means for recording when said inhibiting means inhibits said infusion means.

173. A programmable infusion system in accordance with claim 149, wherein said recording means is coupled to said telemetry means, said recording means providing a signal to said telemetry means for telemetering to said telemetry receiving means operationl information pertaining to said inhibiting means as recorded by said recording means.

174. A programmable infusion system in accordance with claim 110, said infusion apparatus further comprising means for generating a distinctive alarm signal pattern for each of a plurality of improper operational conditions.

175. A programmable infusion system in accordance with claim 174, further comprising means for delivering said alarm signal pattern to said living body subcutaneously.

176. A programmable infusion system in accordance with claim 175, further comprising means for detecting a medication leak, said medication detecting means being coupled to said alarm generating means, wherein one of said improper operational conditions comprises a medication leak out of said medication reservoir.

177. A programmable infusion system in accordance with claim 175, further comprising means for detecting a body fluid leak, said body fluid detecting means being coupled to said alarm generating means, wherein one of said improper operational conditions comprises a leak of body fluids into said infusion apparatus.

178. A programmable infusion system in accordance with claim 175, further comprising means for detecting the rate at which said infusion means is operating, said rate detecting means being coupled to said alarm generating means, wherein one of said improper operational conditions comprises operation of said infusion means at an improper rate.

179. A programmable infusion system in accordance with claim 175, wherein one of said improper operational conditions comprises receiving of a command by said command receiver means which cannot be executed.

180. A programmable infusion system in accordance with claim 175, further comprising battery means for powering said infusion means and means for determining the voltage of said battery means, said voltage determining means being coupled to said alarm generating means, wherein one of said improper operational conditions comprises low battery means voltage.

181. A programmable infusion system in accordance with claim 175, further comprising means for detecting the amount of medication disposed in said reservoir, said medication amount detecting means being coupled to said alarm generating means, wherein one of said improper operational conditions comprises a preselected amount of medication remaining in said medication reservoir.

182. A programmable infusion system in accordance with claim 174, further comprising means for detecting a medication leak, said medication detecting means being coupled to said alarm means, wherein one of said improper operational conditions comprises a medication leak out of said medication reservoir.

183. A programmable infusion system in accordance with claim 174, further comprising means for detecting a body fluid leak, said body fluid detecting means being coupled to said alarm generating means wherein one of said improper operational conditions comprises a leak of body fluids into said infusion apparatus.

184. A programmable infusion system in accordance with claim 174, further comprising means for detecting the rate at which said infusion means is operating, said rate detecting means being coupled to said alarm generating means, wherein one of said improper operational conditions comprises operation of said infusion means at an improper rate.

185. A programmable infusion system in accordance with claim 174, wherein one of said improper operational conditions comprises receiving of a command by said command receiver means which cannot be executed.

186. A programmable infusion system in accordance with claim 174, further comprising battery means for powering said infusion means and means for determining the voltage of said battery means, said voltage determining means being coupled to said alarm generating means wherein one of said improper operational conditions comprises low battery means voltage.

187. A programmable infusion system in accordance with claim 174, further comprising means for detecting the amount of medication disposed in said reservoir, said medication amount detecting means being coupled to said alarm generating means, wherein one of said improper operational conditions comprises a preselected amount of medication remaining in said medication reservoir.

188. A programmable infusion system in accordance with claim 174, further comprising means for simulating said improper operational conditions for test purposes.

189. A programmable infusion system in accordance with claim 110, wherein said infusion means includes means for pumping a preselected amount of medication into said living body, said infusion apparatus further comprising means for recording the rate at which pumping is effected by said pump means.

190. A programmable infusion system in accordance with claim 189, wherein said recording means comprises:
means for storing the rate at which said pump means pumps over a preselected time period;
means for storing a programmable input corresponding to a minimum medication infusion rate; and
means for comparing the rate recorded by said first recited storing means to the rate stored in said second recited storing means.

191. A programmable infusion system in accordance with claim 190, further comprising means for providing an alarm signal when said rate recorded by said first recited storing means is less than said programmable input corresponding to said minimum medication infusion rate recorded by said second recited storing means.

192. A programmable infusion system in accordance with claim 191, wherein said recording means is coupled to said telemetry means for telemetering information recorded by said recording means out of said living body.

193. A programmable infusion system in accordance with claim 189, wherein said recording means comprises:
means for storing the rate at which said pump means pumps over a preselected time period; and
means for storing the rate at which said pump means is signalled to pump over said preselected time period.

194. A programmable infusion system in accordance with claim 193, further comprising means for comparing the rates recorded by both said storing means.

195. A programmable infusion system in accordance with claim 194, wherein said comparing means is coupled to said telemetry means for telemetering information outputted by said comparing means out of said living body.

196. A programmable infusion system in accordance with claim 194, further comprising means for providing an alarm signal when the rate at which said pump means pumps is different than the rate at which said pump means is signalled to pump.

197. A programmable infusion system in accordance with claim 193, wherein said recording means is coupled to said telemetry means for telemetering information recorded by said recording means out of said living body.

198. A programmable infusion system in accordance with claim 189, wherein said pump means executes in pulses, said recording means comprising a pulse rate detector comprising:
means for counting the number of times said pump means pumps over a preselected time period, said counting means storing the count;
minimum rate memory means for storing a programmable number input corresponding to a minimum medication infusion rate; and
means for comparing the number counted by said counting means with said programmable number input stored in said minimum rate memory means.

199. A programmable infusion system in accordance with claim 198, further comprising means for providing an alarm signal when said count is less than said programmable number input stored in said minimum rate memory means.

200. A programmable infusion system in accordance with claim 199, wherein said alarm signal comprises a subcutaneous electrical stimulation.

201. A programmable infusion system in accordance with claim 199, wherein said counting means comprises a pressure transducer.

202. A programmable infusion system in accordance with claim 199, wherein said comparing means is coupled to said telemetry means for telemetering information outputted by said comparing means out of said living body.

203. A programmable infusion system in accordance with claim 189, wherein said pump means executes in pulses, said recording means comprising a pulse recorder comprising:
  means for counting the number of times said pump means pumps over a preselected time period, said counting means storing the count; and
  means for counting the number of times said pump means is commanded to pump over said preselected time period.

204. A programmable infusion system in accordance with claim 203, wherein said pulse recorder further comprises means for comparing the numbers recorded by both said counting means.

205. A programmable infusion system in accordance with claim 204, wherein said comparing means is coupled to said telemetry means for telemetering information outputted by said comparing means out of said living body.

206. A programmable infusion system in accordance with claim 203, further comprising means for providing an alarm signal when said numbers recorded by both said counting means are different.

207. A programmable infusion system in accordance with claim 206, wherein said alarm signal comprises a subcutaneous electrical stimulation.

208. A programmable infusion system in accordance with claim 203, wherein said recording means is coupled to said telemetry means for telemetering information recorded by both said counting means out of said living body.

209. A programmable infusion system in accordance with claim 203, wherein said first recited counting means comprises a pressure transducer.

210. A programmable infusion system in accordance with claim 189, wherein said recording means is powered by said implanted power source.

211. A programmable infusion system in accordance with claim 110 further comprising means for maintaining the pressure within said medication reservoir at a pressure level below the internal pressure of said living body.

212. A programmable infusion system in accordance with claim 211, wherein said pressure maintaining means comprises:
  a flexible diaphragm which divides said medication reservoir into a medication chamber and a liquid-vapor pool chamber; and
  a liquid vapor pool disposed within said liquid-vapor pool chamber, the proportion of liquid to vapor in said liquid-vapor pool varying in response to variations in the amount of said selected medication disposed in said medication chamber.

213. A programmable infusion system in accordance with claim 212, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetry receiving means.

214. A programmable infusion system in accordance with claim 213, wherein said switch means is activated by pressure exerted thereon by said flexible diaphragm, said pressure being less than the ambient pressure of said body.

215. A programmable infusion system in accordance with claim 212, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in the said medication chamber by more than a predetermined differential.

216. A programmable infusion system in accordance with claim 215, wherein the volume of said antechamber is less than 10% the volume of said medication chamber.

217. A programmable infusion system in accordance with claim 215, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

218. A programmable infusion system in accordance with claim 110, further comprising means for programmed pumping of fixed-volume pulses of medication into said living body.

219. A programmable infusion system in accordance with claim 110, further comprising means for injecting medication into said medication reservoir, said injecting means being coupled to said telemetering receiver means, and programming means coupled to said telemetry means for indicating when ejection of medication into said medication reservoir is appropriate.

220. A programmable infusion system in accordance with claim 110, wherein said programming means is powered by said supply means.

221. A programmable infusion system for providing medication to a living body of a patient comprising:
  an infusion apparatus for implantation in said living body, said apparatus including
    a medication reservoir for storing selected medication,
    means for infusing said selected medication stored in said medication reservoir into said living body, said infusion means having a fluid handling mechanism for delivering said selected medication and at least one remotely commandable operational characteristic,
    command receiver means coupled to said infusion means for receiving command signals, and
    means for telemetering operational information pertaining to said infusion apparatus out of said living body, said operational information including information about the operation of said fluid handling mechanism of said infusion means;
  command source means external to said living body for transmitting said command signals to be received by said command receiver means; and
  means for receiving said telemetered operational information external to said living body.

222. A programmable infusion system in accordance with claim 221, wherein said fluid handling mechanism comprises means for pumping said selected medication.

223. A programmable infusion system in accordance with claim 222, wherein said pump means further comprises pressure limiting means for controlling the amount of medication pumped by said pump means.

224. A programmable infusion system in accordance with claim 222, wherein said pump means operates in a pulsatile mode.

225. A programmable infusion system in accordance with claim 224, wherein said pump means pumps a fixed volume of said selected medication each time said pump means is pulsed.

226. A programmable infusion system in accordance with claim 222, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means.

227. A programmable infusion system in accordance with claim 226, wherein said variable volume means comprises at least one flexible wall, movement of said at least one flexible wall varying the volume of said variable volume means, and means for moving said at least one flexible wall.

228. A programmable infusion system in accordance with claim 227, further comprising spring means for urging said at least one flexible wall in a manner which decreases the volume of said variable volume means, the magnitude of the force applied to and stored by said spring means increasing as the volume of said variable volume means increases due to the displacement of said at least one flexible wall thereof by said moving means.

229. A programmable infusion system in accordance with claim 228, wherein said at least one flexible wall comprises a bellows assembly having mounted on one end thereof a plate, the other end of said bellows assembly being in communication with said selected medication, the walls of said bellows assembly serving as said spring means.

230. A programmable infusion system in accordance with claim 229, wherein said plate has a surface in contact with said selected medication when drawn into said variable volume means.

231. A programmable infusion system in accordance with claim 230, wherein said bellows assembly is inhibited from moving said plate when the pressure (p) in said variable volume means exceeds the spring force (F) of said bellows assembly divided by the wetted area (A) of said surface of said plate in contact with said selected medication, that is when p>F/A.

232. A programmable infusion system in accordance with claim 229, wherein said plate is magnetizable, said moving means comprising a coil disposed proximate to said plate, said coil selectively radiating a pulsing magnetic field, pulsing of said coil causing said plate to be moved.

233. A programmable infusion system in accordance with claim 232, wherein said plate comprises a permanent magnet.

234. A programmable infusion system in accordance with claim 229, further comprising means for limiting the distance said plate can move in both a volume increasing direction and a volume decreasing direction.

235. A programmable infusion system in accordance with claim 226, wherein said infusion means further comprises:
an interface pressure valve through which said selected medication enters said variable volume means from said medication reservoir, said interface pressure valve being normally closed;
an outlet chamber which is in communication with said living body; and
an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure pulse.

236. A programmable infusion system in accordance with claim 235, wherein said outlet chamber comprises an elastic wall having a fluidic capacitive effect on the flow of said selected medication and a filter element through which liquid flow to the said living body is resisted, said elastic wall and said filter comprising a fluid resistance-capacitance arrangement with respect to said flow of said selected medication from said outlet chamber into said living body.

237. A programmable infusion system in accordance with claim 225, further comprising means for feeding said selected medication into said living body from said pump means in a flow which decays exponentially over time.

238. A programmable infusion system in accordance with claim 237, wherein said feeding means comprises a mechanical resistance (R) and a mechanical capacitance (C) circuit resulting in an exponentially decaying outflow of medication for each said fixed volume pulse.

239. A programmable infusion system in accordance with claim 226, wherein said infusion means further comprises an outlet chamber which is in communication with said living body, said pump means expelling said selected medication into said outlet chamber, and means for monitoring the operation of said pump means, said monitoring means being disposed in said outlet chamber and providing a signal in response to a pressure pulse in said outlet chamber caused by said pump means, said monitoring means being operably coupled to said telemetry means.

240. A programmable infusion system in accordance with claim 239, wherein said monitoring means comprises a pressure transducer.

241. A programmable infusion system in accordance with claim 239, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

242. A programmable infusion system in accordance with claim 241, further comprising second means for indicating the operation of said pump means wherein a signal is provided by said monitoring means absent a decrease in volume of said variable volume means, said second indicating means being operably coupled to said telemetry means.

243. A programmable infusion system in accordance with claim 222, further comprising means for monitoring the operation of said pump means, said monitoring means being operably coupled to said telemetry means.

244. A programmable infusion system in accordance with claim 243, wherein said monitoring means comprises pressure sensing means disposed in the path of flow of said selected medication into said lining body, said pressure sensing means providing a signal in response to a pressure pulse in said path of flow.

245. A programmable infusion system in accordance with claim 244, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

246. A programmable infusion system in accordance with claim 245, further comprising second means for indicating the operation of said pump means when a signal is provided by said monitoring means absent a decrease in volume of said variable volume means, said second indicating means being operably coupled to said telemetry means.

247. A programmable infusion system in accordance with claim 221, wherein one of said command signals transmitted by said command source means comprises a signal which corresponds to a selected operational rate at which said infusion means will infuse said selected medication into said living body.

248. A programmable infusion system in accordance with claim 221, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of said medication dose inputs.

249. A programmable infusion system in accordance with claim 248, wherein said infusion apparatus further comprises electronic control means coupled to said infusion means and said command receiver means, said electronic control means including means for mainitaining a history of the infusion rate at which said infusion means has operated, said electronic control means including means for precluding the infusion of said selected medication by said infusion means if said rate requested by said patient programming unit exceeds a predetermined safe medication infusion rate based on said maintained history.

250. A programmable infusion system in accordance with claim 249, wherein said electronic control means is coupled to said telemetry means, said patient programming unit including means for indicating to said patient if said selected infusion rate exceeds said predetermined safe medication infusion rate, said electronic control means selectively sending a signal to said indicating means via said telemetry means and said telemetry receiving means, said telemetry receiving means being coupled to said indicating means.

251. A programmable infusion system in accordance with claim 248, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

252. A programmable infusion system in accordance with claim 221, further comprising means for selectively supplying power to said command receiver means, said supply means being coupled to an external power source, said supply means being external to said living body, said infusion means being powered by an implanted power source.

253. A programmable infusion system, in accordance with claim 252, wherein said supply means provides an alternating field.

254. A programmable infusion system, in accordance with claim 253, wherein said infusion apparatus further comprises detector means for detecting said alternating field and for converting the same into electrical energy, said detecting means being coupled to said command receiver.

255. A programmable infusion system in accordance with claim 254, wherein said infusion apparatus further comprises means for rectifying said electrical energy into a d.c. power signal.

256. A programmable infusion system in accordance with claim 255, wherein said d.c. power signal is coupled to said implanted power source to effect the charging thereof.

257. A programmable infusion system in accordance with claim 255, wherein said telemetry means is coupled to said rectifier means and is powered by said d.c. power signal.

258. A programmable infusion system in accordance with claim 252, wherein said telemetry means is also supplied power by said supply means.

259. A programmable infusion system in accordance with claim 252, further comprising means for selectively recharging said implanted power source, said recharging means being powered by said supply means.

260. A programmable infusion system in accordance with claim 221, wherein one of said at least one remotely commandable operational characteristic comprises an infusion rate variable on command, said infusion apparatus further comprising means for inhibiting said infusion apparatus further comprising means for inhibiting said infusion means from infusing said selected medication if a preselected medication infusion rate is exceeded by a commanded infusion rate, said inhibiting means being operably coupled to said infusion means.

261. A programmable infusion system in accordance with claim 260, wherein said inhibiting means comprises at least one means for defining a fixed infusion rate limit.

262. A programmable infusion system in accordance with claim 261, wherein said at least one means for defining a fixed infusion rate limit is hardwired.

263. A programmable infusion system in accordance with claim 260, wherein said preselected medication infusion rate is remotely selectable.

264. A programmable infusion system in accordance with claim 260, wherein said preselected medication infusion rate comprises a remotely selectable rate and a fixed rate, said remotely selectable rate being limited by said fixed rate.

265. A programmable infusion system in accordance with claim 264, wherein said inhibiting means comprises:
at least one programmable rate memory unit coupled to said command receiver means, each of said at least one programmable rate memory units for receiving and storing an infusion rate input command corresponding to said remotely selectable rate;
at least one limit control unit, each of said at least one limit control units providing a fixed rate limit; and
means for comparing each of said infusion rate input commands to a corresponding said fixed rate limit, infusion of said medication at a rate exceeding said fixed rate limit being inhibited.

266. A programmable infusion system in accordance with claim 265, further comprising command decoder means for coupling each of said at least one said programmable rate memory units to command receiver means, said command decoder means for decoding said command signals received by said command receiver means into said infusion rate inputs for receipt by and storage in corresponding said at least one programmable rate memory units.

267. A programmable infusion system in accordance with claim 265, wherein each of said at least one limit control units are hardwired.

268. A programmable infusion system in accordance with claim 265, further comprising means for generating an alarm signal when any infusion rate input command exceeds a corresponding fixed rate limit.

269. A programmable infusion system in accordance with claim 265, wherein said inhibiting means precludes infusion of said medication by said infusion means when the selected said commandable infusion rate exceeds said preselected medication infusion rate during a window of time of a predetermined length which shifts continuously.

270. A programmable infusion system in accordance with claim 260, wherein said inhibiting means precludes infusion of said medication by said infusion means when the selected said commandable infusion rate exceeds said preselected infusion rate during a fixed window of time which shifts continuously.

271. A programmable infusion system in accordance with claim 260, wherein said fluid handling mechanism of said infusion means includes a pump means which executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

272. A programmable infusion system in accordance with claim 271, wherein said memory rate unit also records the number of pulses which have been inhibited and causes said pump means of said fluid handling mechanism to execute said pulses when said pulses can be subtracted as a result of the elapse of time from said dose limit number stored in said programmable memory rate unit.

273. A programmable infusion system in accordance with claim 271, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

274. A programmable infusion system in accordance with claim 273, wherein said rate memory unit also records the number of pulses which have been inhibited and causes said pump means of said fluid handling mechanism to execute said pulses when said pulses can be subtracted from both said dose limit numbers stored in said programmable memory rate unit.

275. A programmable infusion system in accordance with claim 274, wherein said inhibiting means further comprises at least one fixed infusion rate limit which limits the total maximum infusion rate of said infusion means.

276. A programmable infusion system in accordance with claim 275, wherein said fixed infusion rate limit is hardwired.

277. A programmable infusion system in accordance with claim 273, further comprising means for generating an alarm signal when any commanded infusion rate results in the inhibiting of pulsing of said pump means by said inhibiting means.

278. A programmable infusion system in accordance with claim 277, wherein said alarm signal comprises a subcutaneous electrical stimulation.

279. A programmable infusion system in accordance with claim 273, further comprising command decoder means for coupling said command receiver means to said programmable memory rate unit, said command decoder means for decoding said command signals received by said command receiver means into said first and second maximum numbers of infusion pulses.

280. A programmable infusion system in accordance with claim 260, wherein said inhibiting means is operably coupled to said telemetry means, said inhibiting means providing a signal to said telemetry means for telemetering to said telemetry receiving means operational information pertaining to the functions of said inhibiting means.

281. A programmable infusion system in accordance with claim 260, further comprising means for generating an alarm signal when said inhibiting means inhibits said infusion means.

282. A programmable infusion system in accordance with claim 260, further comprising means for recording when said inhibiting means inhibits said infusion means.

283. A programmable infusion system in accordance with claim 282, wherein said recording means is coupled to said telemetry means, said recording means providing a signal to said telemetry means for telemetering to said telemetry receiving means operational information pertaining to said inhibiting means as recorded by said recording means.

284. A programmable infusion system in accordance with claim 221, said infusion apparatus further comprising means for generating a distinctive alarm signal pattern for each of a plurality of improper operational conditions.

285. A programmable infusion system in accordance with claim 284, further comprising means for delivering said alarm signal pattern to said living body subcutaneously.

286. A programmable infusion system in accordance with claim 285, further comprising means for detecting a medication leak, said medication detecting means being coupled to said alarm generating means, wherein one of said improper operational conditions comprises a medication leak out of said medication reservoir.

287. A programmable infusion system in accordance with claim 285, further comprising means for detecting a body fluid leak, said body fluid detecting means being coupled to said alarm generating means, wherein one of said improper operational conditions comprises a leak of body fluids into said infusion apparatus.

288. A programmable infusion system in accordance with claim 285, further comprising means for detecting the rate at which said infusion means is operating, said rate detecting means being coupled to said alarm generating means, wherein one of said improper operational conditions comprises operation of said infusion means at an improper rate.

289. A programmable infusion system in accordance with claim 285, wherein one of said improper operational conditions comprises receiving of a command by said command receiver means which cannot be executed.

290. A programmable infusion system in accordance with claim 285, further comprising battery means for powering said infusion means and means for determining the voltage of said battery means, said voltage determining means being coupled to said alarm generating means, wherein one of said improper operational conditions comprises low battery means voltage.

291. A programmable infusion system in accordance with claim 285, further comprising means for detecting the amount of medication disposed in said reservoir, said medication amount detecting means being coupled to said alarm generating means wherein one of said improper operational conditions comprises a preselected amount of medication remaining in said medication reservoir.

292. A programmable infusion system in accordance with claim 284, further comprising means for detecting a medication leak, said medication detecting means being coupled to said alarm means, wherein one of said improper operational conditions comprises a medication leak out of said medication reservoir.

293. A programmable infusion system in accordance with claim 284, further comprising means for detecting a body fluid leak, said body fluid detecting means being coupled to said alarm generating means, wherein one of said improper operational conditions comprises a leak of body fluids into said infusion apparatus.

294. A programmable infusion system in accordance with claim 284, further comprising means for detecting the rate at which said infusion means is operating, said rate detecting means being coupled to said alarm generating means, wherein one of said improper operational conditions comprises operation of said infusion means at an improper rate.

295. A programmable infusion system in accordance with claim 284, wherein one of said improper operational conditions comprises receiving of a command by said command receiver means which cannot be executed.

296. A programmable infusion system in accordance with claim 284, further comprising battery means for powering said infusion means and means for determining the voltage of said battery means, said voltage determining means being coupled to said alarm generating means wherein one of said improper operational conditions comprises low battery means voltage.

297. A programmable infusion system in accordance with claim 284, further comprising means for detecting the amount of medication disposed in said reservoir, said medication amount detecting means being coupled to said alarm generating means wherein one of said improper operational conditions comprises a preselected amount of medication remaining in said medication reservoir.

298. A programmable infusion system in accordance with claim 284, further comprising means for simulating said improper operational conditions for test purposes.

299. A programmable infusion system in accordance with claim 221, wherein said fluid handling mechanism includes means for pumping a preselected amount of medication into said living body, said infusion apparatus further comprising means for recording the rate at which pumping is effected by said pump means.

300. A programmable infusion system in accordance with claim 299, wherein said recording means comprises:
means for storing the rate at which said pump means pumps over a preselected time period;
means for storing a programmable input corresponding to a minimum medication infusion rate; and
means for comparing the rate recorded by said first recited storing means to the rate stored in said second recited storing means.

301. A programmable infusion system in accordance with claim 300, further comprising means for providing an alarm signal when said rate recorded by said first recited storing means is less than said programmable input corresponding to said minimum medication infusion rate recorded by said second recited storing means.

302. A programmable infusion system in accordance with claim 300, wherein said recording means is coupled to said telemetry means for telemetering information recorded by said recording means out of said living body.

303. A programmable infusion system in accordance with claim 299, wherein said recording means comprises:
means for storing the rate at which said pump means pumps over a preselected time period; and
means for storing the rate at which said pump means is signalled to pump over said preselected time period.

304. A programmable infusion system in accordance with claim 303, further comprising means for comparing the rates recorded by both said storing means.

305. A programmable infusion system in accordance with claim 304, wherein said comparing means is coupled to said telemetry means for telemetering information outputted by said comparing means out of said living body.

306. A programmable infusion system in accordance with claim 304, further comprising means for providing an alarm signal when the rate at which said pump means pumps is different than the rate at which said pump means is signalled to pump.

307. A programmable infusion system in accordance with claim 303, wherein said recording means is coupled to said telemetry means for telemetering information recorded by said recording means out of said living body.

308. A programmable infusion system in accordance with claim 299, wherein said pump means executes in pulses, said recording means comprising a pulse rate detector comprising:
means for counting the number of times said pump means pumps over a preselected time period, said counting means storing the count;
minimum rate memory means for storing a programmable number input corresponding to a minimum medication infusion rate; and
means for comparing the number counted by said counting means with said programmable number input stored in said minimum rate memory means.

309. A programmable infusion system in accordance with claim 308, further comprising means for providing an alarm signal when said count is less than said programmable number input stored in said minimum rate memory means.

310. A programmable infusion system in accordance with claim 309, wherein said alarm signal comprises a subcutaneous electrical stimulation.

311. A programmable infusion system in accordance with claim 309, wherein said counting means comprises a pressure transducer.

312. A programmable infusion system in accordance with claim 308, wherein said comparing means is coupled to said telemetry means for telemetering information outputted by said comparing means out of said living body.

313. A programmable infusion system in accordance with claim 309, wherein said pump means executes in pulses, said recording means comprising a pulse recorder comprising:
means for counting the number of times said pump means pumps over a preselected time period, said counting means storing the count; and
means for counting the number of times said pump means is commanded to pump over said preselected time period.

314. A programmable infusion system in accordance with claim 313, wherein said pulse recorder further comprises means for comparing the numbers recorded by both said counting means.

315. A programmable infusion system in accordance with claim 314, wherein said comparing means is coupled to said telemetry means for telemetering information outputted by said comparing means out of said living body.

316. A programmable infusion system in accordance with claim 315, further comprising means for providing an alarm signal when said numbers recorded by both said counting means are different.

317. A programmable infusion system in accordance with claim 316, wherein said alarm signal comprises a subcutaneous electrical stimulation.

318. A programmable infusion system in accordance with claim 315, wherein said recording means is coupled to said telemetry means for telemetering information recorded by both said counting means out of said living body.

319. A programmable infusion system in accordance with claim 315, wherein said first recited counting means comprises a pressure transducer.

320. A programmable infusion system in accordance with claim 221, further comprising means for maintaining the pressure within said medication reservoir at a pressure level below the internal pressure of said living body.

321. A programmable infusion system in accordance with claim 320, wherein said pressure maintaining means comprises:
a flexible diaphragm which divides said medication reservoir into a medication chamber and a liquid-vapor pool chamber; and
a liquid vapor pool disposed within said liquid-vapor pool chamber, the proportion of liquid to vapor in said liquid-vapor pool varying in response to variations in the amount of said selected medication disposed in said medication chamber.

322. A programmable infusion system in accrodance with claim 321, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetry receiving means.

323. A programmable infusion system in accordance with claim 322, wherein said switch means is activated by pressure exerted thereon by said flexible diaphragm, said pressure being less than the ambient pressure of said body.

324. A programmable infusion system in accordance with claim 321, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in said medication chamber by more than a predetermined differential.

325. A programmable infusion system in accordance with claim 324, wherein the volume of said antechamber is less than 10% the volume of said medication chamber.

326. A programmable infusion system in accordance with claim 324, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

327. A programmable infusion system in accordance with claim 221, further comprising means for programmed pumping of fixed-volume pulses of medication into said living body.

328. A programmable infusion system for providing medication to a living body of a patient comprising:
- an infusion apparatus for implantation in said living body, said apparatus including
    - a medication reservoir for storing selected medication,
    - means for infusing said selected medication stored in said medication reservoir into said living body, said infusion means having an infusion rate variable upon command,
    - command receiver means coupled to said infusion means for receiving command signals, and
    - means for inhibiting said infusion means for infusing said selected medication if a preselected medication infusion rate is exceeded, said inhibiting means being operably coupled to said infusion means; and
- command source means external to said living body for transmitting said command signals to be received by said command receiver means.

329. A programmable infusion system in accordance with claim 328, wherein said inhibiting means comprises at least one means for defining a fixed infusion rate limit.

330. A programmable infusion system in accordance with claim 329, wherein said at least one means for defining a fixed infusion rate limit is hardwired.

331. A programmable infusion system in accordance with claim 328, wherein said preselected medication infusion rate is remotely selectable.

332. A programmable infusion system in accordance with claim 328, wherein said preselected medication infusion rate comprises a remotely selectable rate and a fixed rate, said remotely selectable rate being limited by said fixed rate.

333. A programmable infusion system in accordance with claim 332, wherein said inhibiting means comprises:
- at least one programmable rate memory unit coupled to said command receiver means, each of said at least one programmable rate memory units for receiving and storing an infusion rate input command corresponding to said remotely selectable rate;
- at least one limit control unit, each of said at least one limit control units providing a fixed rate limit; and
- means for comparing each of said infusion rate input commands to a corresponding said fixed rate limit, infusion of said medication at a rate exceeding said fixed rate limit being inhibited.

334. A programmable infusion system in accordance with claim 333, further comprising command decoder means for coupling each of said at least one programmable rate memory units to said command receiver means, said command decoder means for decoding said command signals received by said command receiver means into said infusion rate inputs for receipt by and storage in corresponding said at least one programmable rate memory units.

335. A programmable infusion system in accordance with claim 333, wherein each of said at least one limit control units is hardwired.

336. A programmable infusion system in accordance with claim 333, further comprising means for generating an alarm signal when any infusion rate input command exceeds a corresponding fixed rate limit.

337. A programmable infusion system in accordance with claim 333, wherein said inhibiting means precludes infusion of said medication by said infusion means when the selected said commandable infusion rate exceeds said preselected medication infusion rate during a window of time of a predetermined length which shifts continuously.

338. A programmable infusion system in accordance with claim 328, wherein said inhibiting means precludes infusion of said medication by said infusion means when the selected said commandable infusion rate exceeds said preselected medication infusion rate during a window of time of a predetermined length which shifts continuously.

339. A programmable infusion system in accordance with claim 328, wherein said infusion means includes a pump means which executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

340. A programmable infusion system in accordance with claim 339, wherein said memory rate unit also records the number of pulses which have been inhibited and causes said pump means of said infusion means to execute said pulses when said pulses can be subtracted as a result of the elapse of time from said dose limit number stored in said programmable memory rate unit.

341. A programmable infusion system in accordance with claim 339, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

342. A programmable infusion system in accordance with claim 341, wherein said rate memory unit also records the number of pulses which have been inhibited and causes said pump means of said infusion means to execute said pulses when said pulses can be subtracted from both said dose limit numbers stored in said programmable memory rate unit.

343. A programmable infusion system in accordance with claim 342, wherein said inhibiting means further comprises at least one fixed infusion rate limit which limits the total maximum infusion rate of said infusion means.

344. A programmable infusion system in accordance with claim 343, wherein said fixed infusion rate limit is hardwired.

345. A programmable infusion system in accordance with claim 341, further comprising means for generating an alarm signal when any commanded infusion rate results in the inhibiting of pulsing of said pump means by said inhibiting means.

346. A programmable infusion system in accordance with claim 345, wherein said alarm signal comprises a subcutaneous electrical stimulation.

347. A programmable infusion system in accordance with claim 341, further comprising command decoder means for coupling said command receiver means to said programmable memory rate unit, said command decoder means for decoding said command signals received by said command receiver means into said first and second maximum numbers of infusion pulses.

348. A programmable infusion system in accordance with claim 328, further comprising means for telemetering operational information pertaining to said infusion apparatus out of said living body, said operational information including information pertaining to the functions of said inhibiting means, and means for receiving said telemetered operational information external to said living body.

349. A programmable infusion system in accordance with claim 328, wherein one of said command signals transmitted by said command source means comprises a signal which corresponds to a selected operational rate at which said infusion means will infuse said selected medication into said living body.

350. A programmable infusion system in accordance with claim 328, further comprising means for telemetering operational information pertaining to said infusion apparatus out of said living body, and means for receiving said telemetered operational information external to said living body, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of said medication dose inputs.

351. A programmable infusion system in accordance with claim 350, wherein said infusion apparatus further comprises electronic control means coupled to said infusion means and said command receiver means, said electronic control means including means for maintaining a history of the infusion rate at which said infusion means has operated, said electronic control means including means for precluding the infusion of said selected medication by said infusion means if said rate requested by said patient programming unit exceeds a predetermined safe medication infusion rate based on said maintained history.

352. A programmable infusion system in accordance with claim 351, wherein said electronic control means is coupled to said telemetry means, said patient programming unit including means for indicating to said patient if said selected infusion rate exceeds said predetermined safe medication infusion rate, said electronic control means selectively sending a signal to said indicating means via said telemetry means and said telemetry receiving means, said telemetry receiving means being coupled to said indicating means.

353. A programmable infusion system in accordance with claim 331, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

354. A programmable infusion system in accordance with claim 328, further comprising means for selectively supplying power to said command receiver means, said supply means being coupled to an external power source, said supply means being external to said living body, said infusion means being powered by an implanted power source.

355. A programmable infusion system, in accordance with claim 344, wherein said supply means provides an alternating field.

356. A programmable infusion system, in accordance with claim 355, wherein said infusion apparatus further comprises detector means for detecting said alternating field and for converting the same into electrical energy, said detecting means being coupled to said command receiver.

357. A programmable infusion system in accordance with claim 356, wherein said infusion apparatus further comprises means for rectifying said electrical energy into a d.c. power signal.

358. A programmable infusion system in accordance with claim 357, wherein said d.c. power signal is coupled to said implanted power source to effect the charging thereof.

359. A programmable infusion system in accordance with claim 357, further comprising means for telemetering operational information pertaining to said infusion apparatus out of said living body, and means for receiving said telemetered operational information external to said living body, said telemetry means being coupled to said rectifier means and being powered by said d.c. power signal.

360. A programmable infusion system in accordance with claim 354, further comprising means for telemetering operational information pertaining to said infusion apparatus out of said living body, and means for receiving said telemetered operational information external to said living body, said telemetry means also being supplied power by said supply means.

361. A programmable infusion system in accordance with claim 354, further comprising means for selectively recharging said implanted power source, said recharging means being powered by said supply means.

362. A programmable infusion system in accordance with claim 328, wherein said infusion means comprises a fluid handling mechanism for delivering said selected medication, said operational information including information about the operation of said fluid handling mechanism.

363. A programmable infusion system in accordance with claim 362, wherein said fluid handling mechanism comprises means for pumping said selected medication.

364. A programmable infusion system in accordance with claim 363, wherein said pump means further comprises pressure limiting means for controlling the amount of medication pumped by said pump means.

365. A programmable infusion system in accordance with claim 364, wherein said pump means operates in a pulsatile mode.

366. A programmable infusion system in accordance with claim 365, wherein said pump means pumps a fixed volume of said selected medication each time said pump means is pulsed.

367. A programmable infusion system in accordance with claim 364, wherein said pump means comprises variable volume means for storing said selected medication within said pump means, an increase in volume of said variable volume means permitting drawing of said selected medication into said pump means, decrease in volume of said variable volume means permitting expulsion of said selected medication from said pump means.

368. A programmable infusion system in accordance with claim 367, wherein said variable volume means comprises at least one flexible wall, movement of said at least one flexible wall varying the volume of said variable volume means, and means for moving said at least one flexible wall.

369. A programmable infusion system in accordance with claim 368, further comprising spring means for urging said at least one flexible wall in a manner which decreases the volume of said variable volume means, the magnitude of the force applied to and stored by said spring means increasing as the volume of said variable volume means increases due to the displacement of said at least one flexible wall thereof by said moving means.

370. A programmable infusion system in accordance with claim 369, wherein said at least one flexible wall comprises a bellows assembly having mounted on one end thereof a plate, the other end of said bellows assembly being in communication with said selected medication, the walls of said bellows assembly serving as said spring means.

371. A programmable infusion system in accordance with claim 370, wherein said plate has a surface in contact with said selected medication when drawn into said variable volume means.

372. A programmable infusion system in accordance with claim 371, wherein said bellows assembly is inhibited from moving said plate when the pressure (p) in said variable volume means exceeds the spring force (F) of said bellows assembly divided by the wetted area (A) of said surface of said plate in contact with said selected medication, that is when $p > F/A$.

373. A programmable infusion system in accordance with claim 370, wherein said plate is magnetizable, said moving means comprising a coil disposed proximate to said plate, said coil selectively radiating a pulsing magnetic field, pulsing of said coil causing said plate to be moved.

374. A programmable infusion system in accordance with claim 373, wherein said plate comprises a permanent magnet.

375. A programmable infusion system in accordance with claim 370, further comprising means for limiting the distance said plate can move in both a volume increasing direction and a volume decreasing direction.

376. A programmable infusion system in accordance with claim 367, wherein said infusion means further comprises:
an interface pressure valve through which said selected medication enters said variable volume means from said medication reservoir, said interface pressure valve being normally closed;
an outlet chamber which is in communication with said living body; and
an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure pulse.

377. A programmable infusion system in accordance with claim 376, wherein said outlet chamber comprises an elastic wall having a fluidic capacitive effect on the flow of said selected medication and a filter element through which liquid flow to the said living body is resisted, said elastic wall and said filter comprising a fluid resistance-capacitance arrangement with respect to said flow of said selected medication from said outlet chamber into said living body.

378. A programmable infusion system in accordance with claim 366, further comprising means for feeding said selected medication into said living body from said pump means in a flow which decays exponentially over time.

379. A programmable infusion system in accordance with claim 378, wherein said feeding means comprises a mechanical resistance (R) and a mechanical capacitance (C) circuit resulting in an exponentially decaying outflow of medication for each said fixed volume pulse.

380. A programmable infusion system in accordance with claim 367, further comprising means for telemetering operational information pertaining to said infusion apparatus out of said living body, and means for receiving said telemetered operational information external to said living body, wherein said infusion means further comprises an outlet chamber which is in communication with said living body, said pump means expelling said selected medication into said outlet chamber; and means for monitoring the operation of said pump means, said monitoring means being disposed in said outlet chamber and providing a signal in response to a pressure pulse in said outlet chamber caused by said pump means, said monitoring means being operably coupled to said telemetry means.

381. A programmable infusion system in accordance with claim 380, wherein said monitoring means comprises a pressure transducer.

382. A programmable infusion system in accordance with claim 380, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

383. A programmable infusion system in accordance with claim 382 further comprising second means for indicating the operation of said pump means when a signal is provided by said monitoring means absent a decrease in volume of said variable volume means, said second indicating means being operably coupled to said telemetry means.

384. A programmable infusion system in accordance with claim 363, further comprising means for telemetering operational information pertaining to said infusion apparatus out of said living body, means for receiving said telemetered operational information external to said living body, and means for monitoring the operation of said pump means, said monitoring means being operably coupled to said telemetry means.

385. A programmable infusion system in accordance with claim 384 wherein said monitoring means comprises pressure sensing means disposed in the path of flow of said selected medication into said living body, said pressure sensing means providing a signal in response to a pressure pulse in said path of flow.

386. A programmable infusion system in accordance with claim 385, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

387. A programmable infusion system in accordance with claim 386, further comprising second means for indicating the operation of said pump means when a signal is provided by said monitoring means absent a decrease in volume of said variable volume means, said second indicating means being operably coupled to said telemetry means.

388. A programmable infusion system in accordance with claim 328, said infusion apparatus further comprising means for generating a distinctive alarm signal pattern for each of a plurality of improper operational conditions.

389. A programmable infusion system in accordance with claim 388, further comprising means for delivering said alarm signal pattern to said living body subcutaneously.

390. A programmable infusion system in accordance with claim 389, further comprising means for detecting a medication leak, said medication detection means being coupled to said alarm generating means, wherein one of said improper operational conditions comprises a medication leak out of said medication reservoir.

391. A programmable infusion system in accordance with claim 389, further comprising means for detecting a body fluid leak, said body fluid detecting means being coupled to said alarm means wherein one of said improper operational conditions comprises a leak of body fluids into said infusion apparatus.

392. A programmable infusion system in accordance with claim 389, further comprising means for detecting the rate at which said infusion means is operating, said rate detecting means being coupled to said alarm generating means, wherein one of said improper operational conditions comprises operation of said infusion means at an improper rate.

393. A programmable infusion system in accordance with claim 389, wherein one of said improper operational conditions comprises receiving of a command by said command receiver means which cannot be executed.

394. A programmable infusion system in accordance with claim 389, further comprising battery means for powering said infusion means and means for determining the voltage of said battery means, said voltage detecting means being coupled to said alarm generating means, wherein one of said improper operational conditions comprises low battery means voltage.

395. A programmable infusion system in accordance with claim 389, further comprising means for detecting the amount of medication disposed in said reservoir, said medication amount detecting means being coupled to said alarm generating means, wherein one of said improper operational conditions comprises a preselected amount of medication remaining in said medication reservoir.

396. A programmable infusion system in accordance with claim 388, further comprising means for detecting a medication leak, said medication detecting means being coupled to said alarm means, wherein one of said improper operational conditions comprises a medication leak out of said medication reservoir.

397. A programmable infusion system in accordance with claim 388, further comprising means for detecting a body fluid leak, said body fluid detecting means being coupled to said alarm generating means, wherein one of said improper operational conditions comprises a leak of body fluids into said infusion apparatus.

398. A programmable infusion system in accordance with claim 388, further comprising means for detecting the rate at which said infusion means is operating, said rate detecting means being coupled to said alarm generating means, wherein one of said improper operational conditions comprises operation of said infusion means at an improper rate.

399. A programmable infusion system in accordance with claim 389, wherein one of said improper operational conditions comprises receiving of a command by said command receiver means which cannot be executed.

400. A programmable infusion system in accordance with claim 388, further comprising battery means for powering said infusion means and means for determining the voltage of said battery means, said voltage determining means being coupled to said alarm generating means wherein one of said improper operational conditions comprises low battery means voltage.

401. A programmable infusion system in accordance with claim 388, further comprising means for detecting the amount of medication disposed in said reservoir, said medication amount detecting, means being coupled to said alarm generating means, wherein one of said improper operational conditions comprises a preselected amount of medication remaining in said medication reservoir.

402. A programmable infusion system in accordance with claim 388, further comprising means for simulating said improper operational conditions for test purposes.

403. A programmable infusion system in accordance with claim 328, wherein said infusion means includes means for pumping a preselected amount of medication into said living body, said infusion apparatus further comprising means for recording the rate at which pumping is effected by said pump means.

404. A programmable infusion system in accordance with claim 403, wherein said recording means comprises:

means for storing the rate at which said pump means pumps over a preselected time period;

means for storing a programmable input corresponding to a minimum medication infusion rate; and means for comparing the rate recorded by said first recited storing means to the rate stored in said second recited storing means.

405. A programmable infusion system in accordance with claim 404, further comprising means for providing an alarm signal when said rate recorded by said first recited storing means is less than said programmable input corresponding to said minimum medication infusion rate recorded by said second recited storing means.

406. A programmable infusion system in accordance with claim 404, further comprising means for telemetering information recorded by said recording means out of said living body, said telemetry means being coupled to said recording means, and means for receiving said telemetered information external to said living body.

407. A programmable infusion system in accordance with claim 403, wherein said recording means comprises:

means for storing the rate at which said pump means pumps over a preselected time period; and means for storing the rate at which said pump means is signalled to pump over said preselected time period.

408. A programmable infusion system in accordance with claim 407, further comprising means for comparing the rates recorded by both said storing means.

409. A programmable infusion system in accordance with claim 408, further comprising means for telemetering information outputted by said comparing means out of said living body, said comparing means being coupled to said telemetry means, and means for receiving said telemetered information external to said living body.

410. A programmable infusion system in accordance with claim 408, further comprising means for providing an alarm signal when the rate at which said pump means pumps is different than the rate at which said pump means is signalled to pump.

411. A programmable infusion system in accordance with claim 407, further comprising means for telemetering information recorded by said recording means out of said living body, said recording means being coupled to said telemetry means, and means for receiving said telemetered information external to said living body.

412. A programmable infusion system in accordance with claim 403, wherein said pump means executes in pulses, said recording means comprising a pulse rate detector comprising:

means for counting the number of times said pump means pumps over a preselected time period, said counting means storing the count;

minimum rate memory means for storing a programmable number input corresponding to a minimum medication infusion rate; and means for comparing the number counted by said counting means with said programmable number input stored in said minimum rate memory means.

413. A programmable infusion system in accordance with claim 412, further comprising means for providing an alarm signal when said count is less than said programmable number input stored in said minimum rate memory means.

414. A programmable infusion system in accordance with claim 413, wherein said alarm signal comprises a subcutaneous electrical stimulation.

415. A programmable infusion system in accordance with claim 413, wherein said counting means comprises a pressure transducer.

416. A programmable infusion system in accordance with claim 413, further comprising means for telemetering information outputted by said comparing means out of said living body, said comparing means being coupled to said telemetry means, and means for receiving said telemetered operational information external to said living body.

417. A programmable infusion system in accordance with claim 403, wherein said pump means executes in pulses, said recording means comprising a pulse recorder comprising:

means for counting the number of times said pump means pumps over a preselected time period, said counting means storing the count; and means for counting the number of times said pump means is commanded to pump over said preselected time period.

418. A programmable infusion system in accordance with claim 417, wherein said pulse recorder further comprises means for comparing the numbers recorded by both said counting means.

419. A programmable infusion system in accordance with claim 418, further comprising means for telemetering information outputted by said comparing means out of said living body, said comparing means being coupled to said telemetry means, and means for receiving said telemetered information external to said living body.

420. A programmable infusion system in accordance with claim 417, further comprising means for providing an alarm signal when said numbers recorded by both said counting means are different.

421. A programmable infusion system in accordance with claim 420, wherein said alarm signal comprises a subcutaneous electrical stimulation.

422. A programmable infusion system in accordance with claim 417, further comprising means for telemetering information recorded by both said counting means out of said living body, said recording means being coupled to said telemetry means, and means for receiving said telemetered information external to said living body.

423. A programmable infusion system in accordance with claim 417, wherein said first recited counting means comprises a pressure transducer.

424. A programmable infusion system in accordance with claim 328, further comprising means for maintaining the pressure within said medication reservoir at a pressure level below the internal pressure of said living body.

425. A programmable infusion system in accordance with claim 424, wherein said pressure maintaining means comprises:

a flexible diaphragm which divides said medication reservoir into a medication chamber and a liquid-vapor pool chamber; and a liquid vapor pool disposed within said liquid-vapor pool chamber, the proportion of liquid to vapor in said liquid-vapor pool varying in response to variations in the amount of said selected medication disposed in said medication chamber.

426. A programmable infusion system in accordance with claim 425, further comprising means for telemetering operational information pertaining to said infusion apparatus out of said living body, and means for receiving said telemetered operational information external to said living body, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetry receiving means.

427. A programmable infusion system in accordance with claim 426 wherein said switch means is activated by pressure exerted thereon by said flexible diaphragm, said pressure being less than the ambient pressure of said body.

428. A programmable infusion system in accordance with claim 425, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in said medication chamber by more than a predetermined differential.

429. A programmable infusion system in accordance with claim 428, wherein the volume of said antechamber is less than 10% the volume of said medication chamber.

430. A programmable infusion system in accordance with claim 428, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

431. A programmable infusion system in accordance with claim 430, further comprising means for programmed pumping of fixed-volume pulses of medication into said living body.

432. A programmable infusion system in accordance with claim 430, further comprising means for telemetering operational information pertaining to said infusion apparatus out of said living body, means for receiving said telemetered operational information external to said living body, and means for injecting medication into said medication reservoir, said injecting means being coupled to said telemetry receiver means, and programming means coupled to said telemetry means for indicating when injection of medication into said medication reservoir is appropriate.

433. A programmable infusion system for providing medication to a living body of a patient comprising:
an infusion apparatus for implantation in said living body, said apparatus including
a medication reservoir for storing selected medication,
means for infusing said selected medication stored in said medication reservoir into said living body, said infusion means having at least one remotely commandable operational characteristic,
command receiver means coupled to said infusion means for receiving command signals, and
means for generating a distinctive alarm signal pattern for each of a plurality of improper operational conditions in said system; and
command source means external to said living body for transmitting said command signals to be received by said command receiver means.

434. A programmable infusion system in accordance with claim 433, further comprising means for delivering said alarm signal pattern to said living body subcutaneously.

435. A programmable infusion system in accordance with claim 433, further comprising means for detecting a medication leak, said medication detecting means being coupled to said alarm generating means, wherein one of said improper operational conditions comprises a medication leak out of said medication reservoir.

436. A programmable infusion system in accordance with claim 433, further comprising means for detecting a body fluid leak, said body fluid detecting means being coupled to said alarm generating means wherein one of said improper operational conditions comprises a leak of body fluids into said infusion apparatus.

437. A programmable infusion system in accordance with claim 433, further comprising means for detecting the rate at which said infusion means is operating, said rate detecting means being coupled to said alarm means, wherein one of said improper operational conditions comprises operation of said infusion means at an improper rate.

438. A programmable infusion system in accordance with claim 433, wherein one of said improper operational conditions comprises receiving of a command by said command receiver means which cannot be executed.

439. A programmable infusion system in accordance with claim 433, further comprising battery means for powering said infusion means and means for determining the voltage of said battery means, said voltage determining means being coupled to said alarm generating means, wherein one of said improper operational conditions comprises low battery means voltage.

440. A programmable infusion system in accordance with claim 433, further comprising means for detecting the amount of medication disposed in said reservoir, said medication amount detecting means being coupled to said alarm generating means, wherein one of said improper operational conditions comprises a preselected amount of medication remaining in said medication reservoir.

441. A programmable infusion system in accordance with claim 433, further comprising means for detecting a medication leak, said medication detecting means being coupled to said alarm means, wherein one of said improper operational conditions comprises a medication leak out of said medication reservoir.

442. A programmable infusion system in accordance with claim 433, further comprising means for detecting a body fluid leak, said body fluid detecting means being coupled to said alarm generating means, wherein one of said improper operational conditions comprises a leak of body fluids into said infusion apparatus.

443. A programmable infusion system in accordance with claim 433, further comprising means for detecting the rate at which said infusion means is operating, said rate detecting means being coupled to said alarm generating means, wherein one of said improper operational conditions comprises operation of said infusion means at an improper rate.

444. A programmable infusion system in accordance with claim 433, wherein one of said improper operational conditions comprises receiving of a command by said command receiver means which cannot be executed.

445. A programmable infusion system in accordance with claim 433, further comprising battery means for powering said infusion means and means for determining the voltage of said battery means, said voltage determining means being coupled to said alarm generating means, wherein one of said improper operational conditions comprises low battery means voltage.

446. A programmable infusion system in accordance with claim 433, further comprising means for detecting the amount of medication disposed in said reservoir, said medication amount detecting means being coupled to said alarm generating means, wherein one of said improper operational conditions comprises a preselected amount of medication remaining in said medication reservoir.

447. A programmable infusion system in accordance with claim 433, further comprising means for simulating said improper operational conditions for test purposes.

448. A programmable infusion system in accordance with claim 433, wherein one of said command signals transmitted by said command source means comprises a signal which corresponds to a selected operational rate at which said infusion means will infuse said selected medication into said living body.

449. A programmable infusion system in accordance with claim 433, further comprising means for telemetering operational information pertaining to said infusion apparatus out of said living body, and means for receiving said telemetered operational information external to said living body, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of said medication dose inputs.

450. A programmable infusion system in accordance with claim 449, wherein said infusion apparatus further comprises electronic control means coupled to said infusion means and said command receiver means, said electronic control means including means for maintaining a history of the infusion rate at which said infusion means has operated, said electronic control means including means for precluding the infusion of said selected medication by said infusion means if said rate requested by said patient programming unit exceeds a predetermined safe medication infusion rate based on said maintained history.

451. A programmable infusion system in accordance with claim 450, wherein said electronic control means is coupled to said telemetry means, said patient programming unit including means for indicating to said patient if said selected infusion rate exceeds said predetermined safe medication infusion rate, said electronic control means selectively sending a signal to said indicating means via said telemetry means and said telemetry receiving means, said telemetry receiving means being coupled to said indicating means.

452. A programmable infusion system in accordance with claim 450, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

453. A programmable infusion system in accordance with claim 434, further comprising means for selectively supplying power to said command receiver means, said supply means being coupled to an external power source, said supply means being external to said living body, said infusion means being powered by an implanted power source.

454. A programmable infusion system, in accordance with claim 453, wherein said supply means provides an alternating field.

455. A programmable infusion system, in accordance with claim 454, wherein said infusion apparatus further comprises detector means for detecting said alternating field and for converting the same into electrical energy, said detecting means being coupled to said command receiver.

456. A programmable infusion system in accordance with claim 455, wherein said infusion apparatus further comprises means for rectifying said electrical energy into a d.c. power signal.

457. A programmable infusion system in accordance with claim 456, wherein said d.c. power signal is coupled to said implanted power source to effect the charging thereof.

458. A programmable infusion system in accordance with claim 456, further comprising means for telemetering operational information pertaining to said infusion apparatus out of said living body, and means for receiving said telemetered operational information external to said living body, said telemetry means being coupled to said rectifier means and being powered by said d.c. power signal.

459. A programmable infusion system in accordance with claim 453, further comprising means for telemetering operational information pertaining to said infusion apparatus out of said living body, and means for receiving said telemetered operational information external to said living body, said telemetry means also being supplied power by said supply means.

460. A programmable infusion system in accordance with claim 453, further comprising means for selectively recharging said implanted power source, said recharging means being powered by said supply means.

461. A programmable infusion system in accordance with claim 433, wherein said infusion means comprises a fluid handling mechanism for delivering said selected medication, said operational information including information about the operation of said fluid handling mechanism.

462. A programmable infusion system in accordance with claim 461, wherein said fluid handling mechanism comprises means for pumping said selected medication.

463. A programmable infusion system in accordance with claim 462, wherein said pump means further comprises pressure limiting means for controlling the amount of medication pumped by said pumping means.

464. A programmable infusion system in accordance with claim 463, wherein said pump means operates in a pulsatile mode.

465. A programmable infusion system in accordance with claim 464, wherein said pump means pumps a fixed volume of said selected medication each time said pump means is pulsed.

466. A programmable infusion system in accordance with claim 463, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means.

467. A programmable infusion system in accordance with claim 466, wherein said variable volume means comprises at least one flexible wall, movement of said at least one flexible wall varying the volume of said variable volume means, and means for moving said at least one flexible wall.

468. A programmable infusion system in accordance with claim 467, further comprising spring means for urging said at least one flexible wall in a manner which decreases the volume of said variable volume means, the magnitude of the force applied to and stored by said spring means increasing as the volume of said variable volume means increases due to the displacement of said at least one flexible wall thereof by said moving means.

469. A programmable infusion system in accordance with claim 468, wherein said at least one flexible wall comprises a bellows assembly having mounted on one end thereof a plate, the other end of said bellows assembly being in communication with said selected medication, the walls of said bellows assembly serving as said spring means.

470. A programmable infusion system in accordance with claim 469, wherein said plate has a surface in contact with said selected medication when drawn into said variable volume means.

471. A programmable infusion system in accordance with claim 470, wherein said bellows assembly is inhibited from moving said plate when the pressure (p) in said variable volume means exceeds the spring force (F) of said bellows assembly divided by the wetted area (A) of said outlet surface of said plate in contact with said selected medication, that is when $p > F/A$.

472. A programmable infusion system in accordance with claim 469, wherein said plate is magnetizable, said moving means comprising a coil disposed proximate to said plate, said coil selectively radiating a pulsing magnetic field, pulsing of said coil causing said plate to be moved.

473. A programmable infusion system in accordance with claim 472, wherein said plate comprises a permanent magnet.

474. A programmable infusion system in accordance with claim 473, further comprising means for limiting the distance said plate can move in both a volume increasing direction and a volume decreasing direction.

475. A programmable infusion system in accordance with claim 466, wherein said infusion means further comprises:
an interface pressure valve through which said selected medication enters said variable volume means from said medication reservoir, said interface pressure valve being normally closed;
an outlet chamber which is in communication with said living body; and
an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure pulse.

476. A programmable infusion system in accordance with claim 475, wherein said outlet chamber comprises an elastic wall having a fluidic capacitive effect on the flow of said selected medication and a filter element through which liquid flow to the said living body is resisted, said elastic wall and said filter comprising a fluid resistance-capacitance arrangement with respect to said flow of said selected medication from said outlet chamber into said living body.

477. A programmable infusion system in accordance with claim 464, further comprising means for feeding said selected medication into said living body from said pump means in a flow which decays exponentially over time.

478. A programmable infusion system in accordance with claim 477, wherein said feeding means comprises a mechanical resistance (R) and a mechanical capacitance (C) circuit resulting in an exponentially decaying outflow of medication for each said fixed volume pulse.

479. A programmable infusion system in accordance with claim 466, further comprising means for telemetering operational information pertaining to said infusion apparatus out of said living body, and means for receiving said telemetered operational information external to said living body, wherein said infusion means further comprises an outlet chamber which is in communication with said living body, said pump means expelling said selected medication into said outlet chamber, and means for monitoring the operation of said pump means, said monitoring means being disposed in said outlet chamber and providing a signal in response to a pressure pulse in said outlet chamber caused by said pump means, said monitoring means being operably coupled to said telemetry means.

480. A programmable infusion system in accordance with claim 479, wherein said monitoring means comprises a pressure transducer.

481. A programmable infusion system in accordance with claim 479, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

482. A programmable infusion system in accordance with claim 481, further comprising second means for indicating the operation of said pump means when a signal is provided by said monitoring means absent a decrease in volume of said variable volume means, said second indicating means being operably coupled to said telemetry means.

483. A programmable infusion system in accordance with claim 482, further comprising means for telemetering operational information pertaining to said infusion apparatus out of said living body, means for receiving said telemetered operational information external to said living body, and means for monitoring the operation of said pump means, said monitoring means being operably coupled to said telemetry means.

484. A programmable infusion system in accordance with claim 483, wherein said monitoring means comprises pressure sensing means disposed in the path of flow of said selected medication into said living body, said pressure sensing means providing a signal in response to a pressure pulse in said path of flow.

485. A programmable infusion system in accordance with claim 484, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease of volume of said variable volume means is not followed by a signal from said monitoring means corresponding to a pressure pulse of said selected medication expelled into said outlet chamber, said first indicating means being operably coupled to said telemetry means.

486. A programmable infusion system in accordance with claim 485, further comprising second means for indicating the operation of said pump means when a signal is provided by said monitoring means absent a decrease in volume of said variable volume means, said second indicating means being operably coupled to said telemetry means.

487. A programmable infusion system in accordance with claim 433, wherein one of said at least one remotely commandable operational characteristic comprises an infusion rate variable on command, said infusion apparatus further comprising means for inhibiting said infusion means from infusing said selected medication if a preselected medication infusion rate is exceeded by a commanded infusion rate, said inhibiting means being operably coupled to said infusion means.

488. A programmable infusion system in accordance with claim 487, wherein said inhibiting means comprises at least one means for defining a fixed infusion rate limit.

489. A programmable infusion system in accordance with claim 488, wherein said at least one means for defining a fixed infusion rate limit is hardwired.

490. A programmable infusion system in accordance with claim 487, wherein said preselected medication infusion rate is remotely selectable.

491. A programmable infusion system in accordance with claim 487, wherein said preselected medication infusion rate comprises a remotely selectable rate and a fixed rate, said remotely selectable rate being limited by said fixed rate.

492. A programmable infusion system in accordance with claim 491, wherein said inhibiting means comprises:
at least one programmable rate memory unit coupled to said command receiver means, each of said at least one programmable rate memory units for receiving and storing an infusion rate input command corresponding to said remotely selectable rate;
at least one limit control unit, each of said at least one limit control units providing a fixed rate limit; and
means for comparing each of said infusion rate input commands to a corresponding said fixed rate limit, infusion of said medication at a rate exceeding said fixed rate limit being inhibited.

493. A programmable infusion system in accordance with claim 492, further comprising command decoder means for coupling each of said at least one programmable rate memory units to said command receiver means, said command decoder means for decoding said command signals received by said command receiver means into said infusion rate inputs for receipt by and storage in corresponding said at least one programmable rate memory units.

494. A programmable infusion system in accordance with claim 492, wherein each of said at least one limit control units is hardwired.

495. A programmable infusion system in accordance with claim 492, further comprising means for generating an alarm signal when any infusion rate input command exceeds a corresponding fixed rate limit.

496. A programmable infusion system in accordance with claim 492, wherein said inhibiting means precludes infusion of said medication by said infusion means when the selected said commandable infusion rate exceeds said preselected medication infusion rate during a window of time of a predetermined length which shifts continuously.

497. A programmable infusion system in accordance with claim 487, wherein said inhibiting means precludes infusion of said medication by said infusion means when the selected said commandable infusion rate exceeds said preselected medication infusion rate during a window of time of a predetermined length which shifts continuously.

498. A programmable infusion system in accordance with claim 487, wherein said infusion means includes a pump means which executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

499. A programmable infusion system in accordance with claim 498, wherein said memory rate unit also records the number of pulses which have been inhibited and causes said pump means of said infusion means to execute said pulses when said pulses can be subtracted as a result of the elapse of time from said dose limit number stored in said programmable memory rate unit.

500. A programmable infusion system in accordance with claim 498, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

501. A programmable infusion system in accordance with claim 500, wherein said rate memory unit also records the number of pulses which have been inhibited and causes said pump means of said infusion means to execute said pulses when said pulses can be subtracted from both said dose limit numbers stored in said programmable memory rate unit.

502. A programmable infusion system in accordance with claim 501, wherein said inhibiting means further comprises at least one fixed infusion rate limit which limits the total maximum infusion rate of said infusion means.

503. A programmable infusion system in accordance with claim 502, wherein said fixed infusion rate limit is hardwired.

504. A programmable infusion system in accordance with claim 500, further comprising means for generating an alarm signal when any commanded infusion rate results in the inhibiting of pulsing of said pump means by said inhibiting means.

505. A programmable infusion system in accordance with claim 504, wherein said alarm signal comprises a subcutaneous electrical stimulation.

506. A programmable infusion system in accordance with claim 500, further comprising command decoder means for coupling said command receiver means to said programmable memory rate unit, said command decoder means for decoding said command signals received by said command receiver means into said first and second maximum numbers of infusion pulses.

507. A programmable infusion system in accordance with claim 487, further comprising means for telemetering operational information pertaining to said infusion apparatus out of said living body, said operational information including information pertaining to the functions of said inhibiting means, and means for receiving said telemetered operational information external to said living body.

508. A programmable infusion system in accordance with claim 433, wherein said infusion means includes means for pumping a preselected amount of medication into said living body, said infusion apparatus further comprising means for recording the rate at which pumping is effected by said pump means.

509. A programmable infusion system in accordance with claim 508, wherein said recording means comprises:
means for storing the rate at which said pump means pumps over a preselected time period;
means for storing a programmable input corresponding to a minimum medication infusion rate; and
means for comparing the rate recorded by said first recited storing means to the rate stored in said second recited storing means.

510. A programmable infusion system in accordance with claim 509, further comprising means for providing an alarm signal when said rate recorded by said first recited storing means is less than said programmable input corresponding to said minimum medication infusion rate recorded by said second recited storing means.

511. A programmable infusion system in accordance with claim 509, further comprising means for telemetering information recorded by said recording means out of said living body, said telemetry means being coupled to said recording means and means for receiving said telemetered information external to said living body.

512. A programmable infusion system in accordance with claim 508, wherein said recording means comprises:
means for storing the rate at which said pump means pumps over a preselected time period; and
means for storing the rate at which said pump means is signalled to pump over said preselected time period.

513. A programmable infusion system in accordance with claim 512, further comprising means for comparing the rates recorded by both said storing means.

514. A programmable infusion system in accordance with claim 513, further comprising means for telemetering information outputted by said comparing means out of said living body, said comparing means being coupled to said telemetry means, and means for receiving said telemeterd information external to said living body.

515. A programmable infusion system in accordance with claim 513, further comprising means for providing an alarm signal when the rate at which said pump means pumps is different than the rate at which said pump means is signalled to pump.

516. A programmable infusion system in accordance with claim 512, further comprising means for telemetering information recorded by said recording means out of said living body, said recording means being coupled to said telemetry means, and means for receiving said telemeterd information external to said living body.

517. A programmable infusion system in accordance with claim 508, wherein said pump means executes in pulses, said recording means comprising a pulse rate detector comprising:
means for counting the number of times said pump means pumps over a preselected time period, said counting means storing the count;
minimum rate memory means for storing a programmable number input corresponding to a minimum medication infusion rate; and
means for comparing the number counted by said counting means with said programmable number input stored in said minimum rate memory means.

518. A programmable infusion system in accordance with claim 517, further comprising means for providing an alarm signal when said count is less than said programmable number input stored in said minimum rate memory means.

519. A programmable infusion system in accordance with claim 518, wherein said alarm signal comprises a subcutaneous electrical stimulation.

520. A programmable infusion system in accordance with claim 518, wherein said counting means comprises a pressure transducer.

521. A programmable infusion system in accordance with claim 518, further comprising means for telemetering information outputted by said comparing means out of said living body, said comparing means being coupled to said telemetry means, and means for receiving said telemetered operational information external to said living body.

522. A programmable infusion system in accordance with claim 508, wherein said pump means executes in pulses, said recording means comprising a pulse recorder comprising:
- means for counting the number of times said pump means pumps over a preselected time period, said counting means storing the count; and
- means for counting the number of times said pump means is commanded to pump over said preselected time period.

523. A programmable infusion system in accordance with claim 522, wherein said pulse recorder further comprises means for comparing the numbers recorded by both said counting means.

524. A programmable infusion system in accordance with claim 523, further comprising means for telemetering information outputted by said comparing means out of said living body, said comparing means being coupled to said telemetry means, and means for receiving said telemetered information external to said living body.

525. A programmable infusion system in accordance with claim 522, further comprising means for providing an alarm signal when said numbers recorded by both said counting means are different.

526. A programmable infusion system in accordance with claim 525, wherein said alarm signal comprises a subcutaneous electrical stimulation.

527. A programmable infusion system in accordance with claim 522, further comprising means for telemetering information recorded by both said counting means out of said living body, said recording means being coupled to said telemetry means, and means for receiving said telemetered information external to said living body.

528. A programmable infusion system in accordance with claim 522, wherein said first recited counting means comprises a pressure transducer.

529. A programmable infusion system in accordance with claim 433, further comprising means for maintaining the pressure within said medication reservoir at a pressure level below the internal pressure of said living body.

530. A programmable infusion system in accordance with claim 529, wherein said pressure maintaining means comprises:
- a flexible diaphragm which divides said medication reservoir into a medication chamber and a liquid-vapor pool chamber; and
- a liquid vapor pool disposed within said liquid-vapor pool chamber, the proportion of liquid to vapor in said liquid-vapor pool varying in response to variations in the amount of said selected medication disposed in said medication chamber.

531. A programmable infusion system in accordance with claim 530, further comprising means for telemetering operational information pertaining to said infusion apparatus out of said living body, and means for receiving said telemetered operational information external to said living body, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetering receiving means.

532. A programmable infusion system in accordance with claim 531, wherein said switch means is activated by pressure exerted thereon by said flexible diaphragm, said pressure being less than the ambient pressure of said body.

533. A programmable infusion system in accordance with claim 530, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in said medication chamber by more than a predetermined differential.

534. A programmable infusion system in accordance with claim 533, wherein the volume of said antechamber is less than 10% the volume of said medication chamber.

535. A programmable infusion system in accordance with claim 534, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

536. A programmable infusion system in accordance with claim 534, further comprising means for programmed pumping of fixed-volume pulses of medication into said living body.

537. A programmable infusion system in accordance with claim 534, further comprising means for telemetering operational information pertaining to said infusion apparatus out of said living body, means for receiving said telemetered operational information external to said living body, and means for injecting medication into said medication reservoir, said injecting means being coupled to said telemetry receiver means, and programming means coupled to said telemetry means for indicating when injection of medication into said medication reservoir is appropriate.

538. A programmable infusion system for providing medication to a living body of a patient comprising:
- an infusion apparatus for implantation in said living body, said apparatus including
  - a medication reservoir for storing selected medication,
  - means for infusing said selected medication stored in said medication reservoir into said living body, said infusion means having at least one remotely commandable operational characteristic and including means for pumping a preselected amount of medication into said living body,
  - means for recording the rate at which pumping is effected by said pump means, and
  - command receiver means coupled to said infusion means for receiving command signals; and
- command source means external to said living body for transmitting said command signals to be received by said command receiver means.

539. A programmable infusion system in accordance with claim 538, wherein said recording means comprises:
- means for storing the rate at which said pump means pumps over a preselected time period;

means for storing a programmable input corresponding to a minimum medication infusion rate; and means for comparing the rate recorded by said first recited storing means to the rate stored in said second recited storing means.

540. A programmable infusion system in accordance with claim 539, further comprising means for providing an alarm signal when said rate recorded by said first recited storing means is less than said programmable input corresponding to said minimum medication infusion rate recorded by said second recited storing means.

541. A programmable infusion system in accordance with claim 539, further comprising means for telemetering information recorded by said recording means out of said living body, said telemetry means being coupled to said recording means, and means for receiving said telemetered information external to said living body.

542. A programmable infusion system in accordance with claim 538, wherein said recording means comprises:

means for storing the rate at which said pump means pumps over a preselected time period; and means for storing the rate at which said pump means is signalled to pump over said preselected time period.

543. A programmable infusion system in accordance with claim 542, further comprising means for comparing the rates recorded by both said storing means.

544. A programmable infusion system in accordance with claim 543, further comprising means for telemetering information outputted by said comparing means out of said living body, said comparing means being coupled to said telemetry means, and means for receiving said telemetered information external to said living body.

545. A programmable infusion system in accordance with claim 543, further comprising means for providing an alarm signal when the rate at which said pump means pumps is different than the rate at which said pump means is signalled to pump.

546. A programmable infusion system in accordance with claim 542, further comprising means for telemetering information recorded by said recording means out of said living body, said recording means being coupled to said telemetry means, and means for receiving said telemetered information external to said living body.

547. A programmable infusion system in accordance with claim 538, wherein said pump means executes in pulses, said recording means comprising a pulse rate detector comprising:

means for counting the number of times said pump means pumps over a preselected time period, said counting means storing the count;

minimum rate memory means for storing a programable number input corresponding to a minimum medication infusion rate; and means for comparing the number counted by said counting means with said programmable number input stored in said minimum rate memory means.

548. A programmable infusion system in accordance with claim 547, further comprising means for providing an alarm signal when said count is less than said programmable number input stored in said minimum rate memory means.

549. A programmable infusion system in accordance with claim 548, wherein said alarm signal comprises a subcutaneous electrical stimulation.

550. A programmable infusion system in accordance with claim 548, wherein said counting means comprises a pressure transducer.

551. A programmable infusion system in accordance with claim 548, further comprising means for telemetering information outputted by said comparing means out of said living body, said comparing means being coupled to said telemetry means, and means for receiving said telemetered operational information external to said living body.

552. A programmable infusion system in accordance with claim 538, wherein said pump means executes in pulses, said recording means comprising a pulse recorder comprising:

means for counting the number of times said pump means pumps over a preselected time period, said counting means storing the count; and means for counting the number of times said pump means is commanded to pump over said preselected time period.

553. A programmable infusion system in accordance with claim 552, wherein said pulse recorder further comprises means for comparing the numbers recorded by both said counting means.

554. A programmable infusion system in accordance with claim 553, further comprising means for telemetering information outputted by said comparing means out of said living body, said comparing means being coupled to said telemetry means, and means for receiving said telemetered information external to said living body.

555. A programmable infusion system in accordance with claim 554, further comprising means for providing an alarm signal when said numbers recorded by both said counting means are different.

556. A programmable infusion system in accordance with claim 555, wherein said alarm signal comprises a subcutaneous electrical stimulation.

557. A programmable infusion system in accordance with claim 554, further comprising means for telemetering information recorded by both said counting means out of said living body, said recording means being coupled to said telemetry means, and means for receiving said telemetered information external to said living body.

558. A programmable infusion system in accordance with claim 554, wherein said first recited counting means comprises a pressure transducer.

559. A programmable infusion system in accordance with claim 538, wherein one of said command signals transmitted by said command source means comprises a signal which corresponds to a selected operational rate at which said infusion means will infuse said selected medication into said living body.

560. A programmable infusion system in accordance with claim 538, further comprising means for telemetering operational information pertaining to said infusion apparatus out of said living body, and means for receiving said telemetered operational information external to said living body, wherein said command source and said telemetry receiving means are embodied in a patient programming unit external to said living body, said patient programming unit having a plurality of operational medication dose inputs each corresponding to a medication infusion rate selectable and requestable by the patient, said patient programming unit for selectively transmitting a command signal corresponding to a selected one of said medication dose inputs.

561. A programmable infusion system in accordance with claim 560, wherein said infusion apparatus further comprises electronic control means coupled to said infusion means and said command receiver means, said electronic control means including means for maintaining a history of the infusion rate at which said infusion means has operated, said electronic control means including means for precluding the infusion of said selected medication by said infusion means if said rate requested by said patient programming unit exceeds a predetermined safe medication infusion rate based on said maintained history.

562. A programmable infusion system in accordance with claim 561, wherein said electronic control means is coupled to said telemetry means, said patient programming unit including means for indicating to said patient if said selected infusion rate exceeds said predetermined safe medication infusion rate, said electric control means selectively sending a signal to said indicating means via said telemetry means and said telemetry receiving means, said telemetry receiving means being coupled to said indicating means.

563. A programmable infusion system in accordance with claim 561, wherein said patient programming unit further comprises annunciator means and visual display means for providing information regarding previously selected medication infusion rates, for indicating whether a proper programming of a presently requested infusion rate has been communicated to said command receiver, and for selectively providing information as to the time and rate of previously selected medication infusion.

564. A programmable infusion system in accordance with claim 538, further comprising means for selectively supplying power to said command receiver means, said supply means being coupled to an external power source, said supply means being external to said living body, said infusion means being powered by an implanted power source.

565. A programmable infusion system, in accordance with claim 564, wherein said supply means provides an alternating field.

566. A programmable infusion system, in accordance with claim 565, wherein said infusion apparatus further comprises detector means for detecting said alternating field and for converting the same into electrical energy, said detecting means being coupled to said command receiver.

567. A programmable infusion system in accordance with claim 566, wherein said infusion apparatus further comprises means for rectifying said electrical energy into a d.c. power signal.

568. A programmable infusion system in accordance with claim 567, wherein said d.c. power signal is coupled to said implanted power source to effect the charging thereof.

569. A programmable infusion system in accordance with claim 567, further comprising means for telemetering operational information pertaining to said infusion apparatus out of said living body, and means for receiving said telemetered operational information external to said living body, said telemetry means being coupled to said rectifier means and being powered by said d.c. power signal.

570. A programmable infusion system in accordance with claim 564, further comprising means for telemetering operational information pertaining to said infusion apparatus out of said living body, and means for receiving said telemetered operational information external to said living body, said telemetry means also being supplied power by said supply means.

571. A programmable infusion system in accordance with claim 564, further comprising means for selectively recharging said implanted power source, said recharging means being powered by said supply means.

572. A programmable infusion system in accordance with claim 538, wherein said infusion means comprises a fluid handling mechanism, said fluid handling mechanism including said pump means, said operational information including information about the operation of said fluid handling mechanism.

573. A programmable infusion system in accordance with claim 572, wherein said pump means further comprises pressure limiting means for controlling the amount of medication pumped by said pump means.

574. A programmable infusion system in accordance with claim 573, wherein said pump means operates in a pulsatile mode.

575. A programmable infusion system in accordance with claim 574, wherein said pump means pumps a fixed volume of said selected medication each time said pump means is pulsed.

576. A programmable infusion system in accordance with claim 575, wherein said pump means comprises variable volume means for storing said selected medication within said at least one, pump means, an increase in volume of said variable volume means permitting drawing of said selected medication into said pump means, a decrease in volume of said variable volume means permitting expulsion of said selected medication from said pump means.

577. A programmable infusion system in accordance with claim 576, wherein said variable volume means comprises at least one flexible wall, movement of said at least one flexible wall varying the volume of said variable volume means and means for moving said at least one flexible wall.

578. A programmable infusion system in accordance with claim 577, further comprising spring means for urging said at least one flexible wall in a manner which decreases the volume of said variable volume means, the magnitude of the force applied to and stored by said spring means increasing as the volume of said variable volume means increases due to the displacement of said at least one flexible wall thereof by said moving means.

579. A programmable infusion system in accordance with claim 578, wherein said at least one flexible wall comprises a bellows assembly having mounted on one end thereof a plate, the other end of said bellows assembly being in communication with said selected medication, the walls of said bellows assembly serving as said spring means.

580. A programmable infusion system in accordance with claim 579, wherein said plate has a surface in contact with said selected medication when drawn into said variable volume means.

581. A programmable infusion system in accordance with claim 580, wherein said bellows assembly is inhibited from moving said plate when the pressure (p) in said variable volume means exceeds the spring force (F) of said bellows assembly divided by the wetted area (A) of said surface of said plate in contact with said selected medication, that is when $p > F/A$.

582. A programmable infusion system in accordance with claim 579, wherein said plate is magnetizable, said moving means comprising a coil disposed proximate to said plate, said coil selectively radiating a pulsing magnetic field, pulsing of said coil causing said plate to be moved.

583. A programmable infusion system in accordance with claim 582, wherein said plate comprises a permanent magnet.

584. A programmable infusion system in accordance with claim 583, further comprising means for limiting the distance said plate can move in both a volume increasing direction and a volume decreasing direction.

585. A programmable infusion system in accordance with claim 576, wherein said infusion means further comprises:
- an interface pressure value through which said selected medication enters said variable volume means from said medication reservoir, said interface pressure valve being normally closed;
- an outlet chamber which is in communication with said living body; and
- an outlet pressure valve located between said variable volume means and said outlet chamber, said outlet pressure valve being normally closed, an increase in volume of said variable volume means causing said interface pressure valve to open and medication to enter said variable volume means, a decrease in volume of said variable volume means causing said outlet pressure valve to open and said interface pressure valve to close, so as to permit medication to enter said outlet chamber as a pressure pulse.

586. A programmable infusion system in accordance with claim 585, wherein said outlet chamber comprises an elastic wall having a fluidic capacitive effect on the flow of said selected medication and a filter element through which liquid flow to the said lining body is resisted, said elastic wall and said filter comprising a fluid resistance-capacitance arrangement with respect to said flow of said selected medication from said outlet chamber into said living body.

587. A programmable infusion system in accordance with claim 575, further comprising means for feeding said selected medication into said living body from said pump means in a flow which decays exponentially over time.

588. A programmable infusion system in accordance with claim 586, wherein said feeding means comprises a mechanical resistance (R) and a mechanical capacitance (C) circuit resulting in an exponentially decaying outflow of medication for each said fixed volume pulse.

589. A programmable infusion system in accordance with claim 576, further comprising means for telemetering operational information pertaining to said infusion apparatus out of said living body, and means for receiving said telemetered operational information external to said living body, wherein said infusion means further comprises an outlet chamber which is in communication with said living body, said pump means expelling said selected medication into said outlet chambers, and means for monitoring the operation of said pump means, said monitoring means being disposed in said outlet chamber and providing a signal in response to a pressure pulse in said outlet chamber caused by said pump means, said monitoring means being operably coupled to said telemetry means.

590. A programmable infusion system in accordance with claim 589, wherein said monitoring means comprises a pressure transducer.

591. A programmable infusion system in accordance with claim 589, further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

592. A programmable infusion system in accordance with claim 591, further comprising second means for indicating the operation of said pump means when a signal is provided by said monitoring means absent a decrease in volume of said variable volume means, said second indicating means being operably coupled to said telemetry means.

593. A programmable infusion system in accordance with claim 582, further comprising means for telemetering operational information pertaining to said infusion apparatus out of said living body, means for receiving said telemetered operational information external to said living body, and means for monitoring the operation of said pump means, said monitoring means being operably coupled to said telemetry means.

594. A programmable infusion system in accordance with claim 593, wherein said monitoring means comprises pressure sensing means disposed in the path of flow of said selected medication into said living body, said pressure sensing means providing a signal in response to a pressure pulse in said path of flow.

595. A programmable infusion system in accordance with claim 594, wherein said pump means comprises variable volume means for storing said selected medication within said pump means, an increase in volume of said variable volume means permitting drawing of said selected medication into said pump means, a decrease in volume of said variable volume means permitting expulsion of said selected medication from said pump means, said system further comprising first means for indicating the operation of said pump means when a decrease in volume of said variable volume means is not followed by a signal from said monitoring means corresponding to a pressure pulse of said selected medication expelled into said outlet chamber, said first indicating means being operably coupled to said telemetry means.

596. A programmable infusion system in accordance with claim 595, further comprising second means for indicating the operation of said pump means when a signal is provided by said monitoring means absent a decrease in volume of said variable volume means, said second indicating means being operably coupled to said telemetry means.

597. A programmable infusion system in accordance with claim 538, wherein one of said at least one remotely commandable operational characteristic comprises an infusion rate variable on command, said infusion apparatus further comprising means for inhibiting said infusion means from infusing said selected medication if a preselected medication infusion rate is exceeded, said inhibiting means being operably coupled to said infusion means.

598. A programmable infusion system in accordance with claim 597, wherein said inhibiting means comprises at least one means for defining a fixed infusion rate limit.

599. A programmable infusion system in accordance with claim 598, wherein said at least one means for defining a fixed infusion rate limit is hardwired.

600. A programmable infusion system in accordance with claim 597, wherein said preselected medication infusion rate is remotely selectable.

601. A programmable infusion system in accordance with claim 597, wherein said preselected medication infusion rate comprises a remotely selectable rate and a fixed rate, said remotely selectable rate being limited by said fixed rate.

602. A programmable infusion system in accordance with claim 601, wherein said inhibiting means comprises:
  at least one programmable rate memory unit coupled to said command receiver means, each of said at least one programmable rate memory units for receiving and storing an infusion rate input command corresponding to said remotely selectable rate;
  at least one limit control unit, each of said at least one limit control units providing a fixed rate limit; and
  means for comparing each of said infusion rate input commands to a corresponding said fixed rate limit, infusion of said medication at a rate exceeding said fixed rate limit being inhibited.

603. A programmable infusion system in accordance with claim 602, further comprising command decoder means for coupling each of said at least one programmable rate memory units to said command receiver means, said command decoder means for decoding said command signals received by said command receiver means into said infusion rate inputs for receipt by and storage in corresponding said at least one programmable rate memory unit.

604. A programmable infusion system in accordance with claim 602, wherein each of said at least on limit control units is hardwired.

605. A programmable infusion system in accordance with claim 602, further comprising means for generating an alarm signal when any infusion rate input command exceeds a corresponding fixed rate limit.

606. A programmable infusion system in accordance with claim 605, wherein said inhibiting means precludes infusion of said medication by said infusion means when the selected said commandable infusion rate exceeds said preselected medication infusion rate during a window of time of a predetermined which shifts continuously.

607. A programmable infusion system in accordance with claim 597, wherein said inhibiting means precludes infusion of said medication by said infusion means when the selected said commandable infusion rate exceeds said preselected medication infusion rate during a window of time of a predetermined length which shifts continuously.

608. A programmable infusion system in accordance with claim 597, wherein said pump means executes in pulses, said inhibiting means comprising a programmable memory rate unit coupled to said command receiver for storing initially a dose limit number corresponding to a first maximum number of infusion pulses preselected as allowable during a first shifting time window of a predetermined length, pulse quantities being subtracted from said number stored in said programmable memory rate unit as infusion pulses are executed by said infusion means, pulse quantities being added to said stored number as time elapses such that said number does not exceed said first maximum number, said subtraction and addition being accomplished in running integral fashion, said inhibiting means not permitting pulsing of said pump means at a rate in excess of the rate represented by said dose limit number stored in said programmable memory rate unit.

609. A programmable infusion system in accordance with claim 608, wherein said memory rate unit also records the number of pulses which have been inhibited and causes said pump means of said infusion means to execute said pulses when said pulses can be subtracted as a result of the elapse of time from said dose limit number stored in said programmable memory rate unit.

610. A programmable infusion system in accordance with claim 608, wherein said programmable memory rate unit also stores initially another dose limit number corresponding to a second maximum number of infusion pulses preselected as allowable during a second shifting time window of a predetermined length, said second shifting time window being longer in length than said first shifting time window, pulse quantities being subtracted from said another dose limit number stored in said programmable memory rate unit as infusion pulses are executed by said infusion means, pulse quantities being added to said another dose limit number as time elapses such that said another dose limit number does not exceed said first maximum number, said subtraction and addition being accomplished in running integral fashion, said inhibiting means not permitting pulsing of said pump means at a rate in excess of the rate represented by said another dose limit number stored in said programmable memory rate unit.

611. A programmable infusion system in accordance with claim 610, wherein said rate memory unit also records the number of pulses which have been inhibited and causes said pump means of said infusion means to execute said pulses when said pulses can be subtracted from both said dose limit numbers stored in said programmable memory rate unit.

612. A programmable infusion system in accordance with claim 611, wherein said inhibiting means further comprises at least one fixed infusion rate limit which limits the total maximum infusion rate of said infusion means.

613. A programmable infusion system in accordance with claim 612, wherein said fixed infusion rate limit is hardwired.

614. A programmable infusion system in accordance with claim 613, further comprising means for generating an alarm signal when any commanded infusion rate results in the inhibiting of pulsing of said pump means by said inhibiting means.

615. A programmable infusion system in accordance with claim 614, wherein said alarm signal comprises a subcutaneous electrical stimulation.

616. A programmable infusion system in accordance with claim 610, further comprising command decoder means for coupling said command receiver means to said programmable memory rate unit, said command decoder means for decoding said command signals received by said command receiver means into said first and second maximum numbers of infusion pulses.

617. A programmable infusion system in accordance with claim 538, further comprising means for telemetering operational information pertaining to said infusion apparatus out of said living body, said operational information including information pertaining to the functions of said inhibiting means, and means for receiving said telemetered operational information external to said living body.

618. A programmable infusion system in accordance with claim 538, said infusion apparatus further comprising means for generating a distinctive alarm signal pattern for each of a plurality of improper operational conditions.

619. A programmable infusion system in accordance with claim 618 further comprising means for delivering said alarm signal pattern to said living body subcutaneously.

620. A programmable infusion system in accordance with claim 619, further comprising means for detecting a medication leak, said medication detecting means being coupled to said alarm generating means, wherein one of said improper operational conditions comprises a medication leak out of said medication reservoir.

621. A programmable infusion system in accordance with claim 619, further comprising means for detecting a body fluid leak, said body fluid detecting means being coupled to said alarm generating means, wherein one of said improper operational conditions comprises a leak of body fluids into said infusion apparatus.

622. A programmable infusion system in accordance with claim 619, further comprising means for detecting the rate at which said infusion means is operating, said rate detecting means being coupled to said alarm generating means, wherein one of said improper operational conditions comprises operation of said infusion means at an improper rate.

623. A programmable infusion system in accordance with claim 619, wherein one of said improper operational conditions comprises receiving of a command by said command receiver means which cannot be executed.

624. A programmable infusion system in accordance with claim 619, further comprising battery means for powering said infusion means and means for determining the voltage of said battery means, said voltage determining means being coupled to said alarm generating means, wherein one of said improper operational conditions comprises low battery means voltage.

625. A programmable infusion system in accordance with claim 619, further comprising means for detecting the amount of medication disposed in said reservoir, said medication amount detecting means being coupled to said alarm generating means, wherein one of said improper operational conditions comprises a preselected amount of medication remaining in said medication reservoir.

626. A programmable infusion system in accordance with claim 618, further comprising means for detecting a medication leak, said medication detecting means being coupled to said alarm means, wherein one of said improper operational conditions comprises a medication leak out of said medication reservoir.

627. A programmable infusion system in accordance with claim 618, further comprising means for detecting a body fluid leak, said body fluid detecting means being coupled to said alarm generating means, wherein one of said improper operational conditions comprises a leak of body fluids into said infusion apparatus.

628. A programmable infusion system in accordance with claim 618, further comprising means for detecting the rate at which said infusion means is operating, said rate detecting means being coupled to said alarm generating means, wherein one of said improper operational conditions comprises operation of said infusion means at an improper rate.

629. A programmable infusion system in accordance with claim 618, wherein one of said improper operational conditions comprises receiving of a command by said command receiver means which cannot be executed.

630. A programmable infusion system in accordance with claim 618, further comprising battery means for powering said infusion means and means for determining the voltage of said battery means, said voltage determining means being coupled to said alarm generating means wherein one of said improper operational conditions comprises low battery means voltage.

631. A programmable infusion system in accordance with claim 618, further comprising means for detecting the amount of medication disposed in said reservoir, said medication amount detecting means being coupled to said alarm generating means wherein one of said improper operational conditions comprises a preselected amount of medication remaining in said medication reservoir.

632. A programmable infusion system in accordance with claim 618, further comprising means for simulating said improper operational conditions for test purposes.

633. A programmable infusion system in accordance with claim 538, further comprising means for maintaining the pressure within said medication reservoir at a pressure level below the internal pressure of said living body.

634. A programmable infusion sytem in accordance with claim 633, wherein said pressure maintaining means comprises:
- a flexible diaphragm which divides said medication reservoir into a medication chamber and a liquid-vapor pool chamber; and
- a liquid vapor pool disposed within said liquid-vapor pool chamber, the proportion of liquid to vapor in said liquid-vapor pool varying in response to variations in the amount of said selected medication disposed in said medication chamber.

635. A programmable infusion system in accordance with claim 634, further comprising means for telemetering operational information pertaining to said infusion apparatus out of said living body, and means for receiving said telemetered operational information external to said living body, said infusion apparatus further comprising switch means disposed within said medication reservoir, said switch means being coupled to said telemetry means and being activated when said flexible diaphragm is disposed in a preselected relationship relative to said switch means, said telemetry means telemetering a signal indicative of such an operational condition to said telemetry receiving means.

636. A programmable infusion system in accordance with claim 635 wherein said switch means is activated by pressure exerted thereon by said flexible diaphragm, said pressure being less than the ambient pressure of said body.

637. A programmable infusion system in accordance with claim 634, said infusion apparatus further comprising an antechamber through which access is gained to said medication reservoir, and a reservoir inlet valve located between said antechamber and said medication chamber, said reservoir inlet valve being operable when the pressure in said antechamber exceeds the pressure in said medication chamber by more than a predetermined differential.

638. A programmable infusion system in accordance with claim 637, wherein the volume of said antechamber is less than 10% the volume of said medication chamber.

639. A programmable infusion system in accordance with claim 637, further comprising an inlet filter means operably disposed between said antechamber and said medication chamber for preventing impurities in said selected medication in said antechamber from passing into said medication chamber when said reservoir inlet valve is opened, said filter means also preventing said selected medication in said medication chamber from rapidly entering said living body in the event of a leak in said inlet valve.

640. A programmable infusion system in accordance with claim 538, further comprising means for programmed pumping of fixed-volume pulses of medication into said living body.

641. A programmable infusion system in accordance with claim 538, further comprising means for telemetering operational information pertaining to said infusion apparatus out of said living body, and means for receiving said telemetered operational information external to said living body, and means for injecting medication into said medication reservoir, said injecting means being coupled to said telemetry receiver means, and programming means coupled to said telemetry means for indicating when injection of medication into said medication reservoir is appropriate.

642. A programmable infusion system in accordance with claim 221, further comprising means for injecting medication into said medication reservoir, said injecting means being coupled to said telemetering receiver means, and programming means coupled to said telemetering means for indicating when ejection of medication into said medication reservoir is appropriate.

* * * * *